(12) United States Patent
Breen

(10) Patent No.: US 9,090,945 B2
(45) Date of Patent: Jul. 28, 2015

(54) MEAN DNA COPY NUMBER OF CHROMOSOMAL REGIONS IS OF PROGNOSTIC SIGNIFICANCE IN CANCER

(75) Inventor: Matthew Breen, Apex, NC (US)

(73) Assignee: North Carolina State University, Raleigh, NC (US)

( * ) Notice: Subject to any disclaimer, the term of this patent is extended or adjusted under 35 U.S.C. 154(b) by 152 days.

(21) Appl. No.: 13/515,614

(22) PCT Filed: Dec. 14, 2010

(86) PCT No.: PCT/US2010/060292
§ 371 (c)(1),
(2), (4) Date: Sep. 28, 2012

(87) PCT Pub. No.: WO2012/115604
PCT Pub. Date: Aug. 30, 2012

(65) Prior Publication Data
US 2013/0011834 A1    Jan. 10, 2013

(51) Int. Cl.
*C12Q 1/68* (2006.01)
*C12N 15/11* (2006.01)

(52) U.S. Cl.
CPC .............. *C12Q 1/6886* (2013.01); *C12N 15/11* (2013.01); *C12Q 1/6806* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | |
|---|---|---|
| 6,251,601 B1 | 6/2001 | Bao et al. |
| 6,905,823 B2 | 6/2005 | Kallioniemi et al. |
| 7,930,104 B2 | 4/2011 | Baker et al. |
| 2007/0275403 A1 | 11/2007 | Morrison et al. |
| 2009/0155805 A1 | 6/2009 | Zhang et al. |
| 2009/0299640 A1 | 12/2009 | Ellis et al. |
| 2009/0324596 A1 | 12/2009 | Kang et al. |

OTHER PUBLICATIONS

Al Mulla et al., "Genetic profiling of stage I and II colorectal cancer may predict metastatic relapse," Modern Pathology. vol. 19, No. 5 pp. 648-658 (2006).
Modiano et al., "Predictive value of p16 or Rb inactivation in a model of naturally occurring canine non-Hodgkin's lymphoma," Leukemia. vol. 21, No. 1 pp. 184-187 (2007).
Notification Concerning Transmittal of International Preliminary Report on Patentability (Chapter I of the Patent Cooperation Treaty) corresponding to International Patent Application No. PCT/US2010/060292 dated Aug. 30, 2012.
Notification of Transmittal of the International Search Report and the Written Opinion of the International Searching Authority, or the Declaration corresponding to International Patent Application No. PCT/US2010/060292 dated Apr. 10, 2012.
Ratcliffe et al., "Proteomic identification and profiling of canine lymphoma patients," Veterinary and Comparative Oncology. vol. 7, No. 2 pp. 92-105 (2009).
Thomas et al., "Chromosome aberrations in canine multicentric lymphomas detected with comparative genomic hybridisation and a panel of single locus probes," British Journal of Cancer. vol. 89, No. 8 pp. 1530-1537 (2003).
European Search Report corresponding to European Patent Application No. 10861217.7-1403/2513340 dated Jun. 3, 2013.
Hahn et al., "Diagnostic and Prognostic Importance of Chromosomal Aberrations Identified in 61 Dogs with Lymphosarcoma," Veterinary Pathology, vol. 31, No. 5, pp. 528-540 (Sep. 1, 1994).
Thomas et al., "A canine cancer-gene microarray for CGH analysis of tumors," Cytogenetic and Genome Research, vol. 102, No. 1-4, pp. 254-260 (2003).
Office Action corresponding with European Patent Applcation No. 10861217.7-1403 dated Apr. 25, 2014.

*Primary Examiner* — James Martinell
(74) *Attorney, Agent, or Firm* — Jenkins, Wilson, Taylor & Hunt, P.A.

(57) ABSTRACT

Methods for predicting a disease free time interval (DFI) for a cancer patient under consideration for initial or further chemotherapy treatment are disclosed. The methods include obtaining a biological sample from a patient and detecting a copy number of chromosome region A1 and/or C2. The mean copy number per cell is correlated with a DFI for the subject. The chemotherapy can include doxorubicin and/or L-asparaginase treatment. Also provided are kits for predicting DFI in a subject with cancer and computer readable storage media for performing the presently disclosed methods.

18 Claims, 16 Drawing Sheets

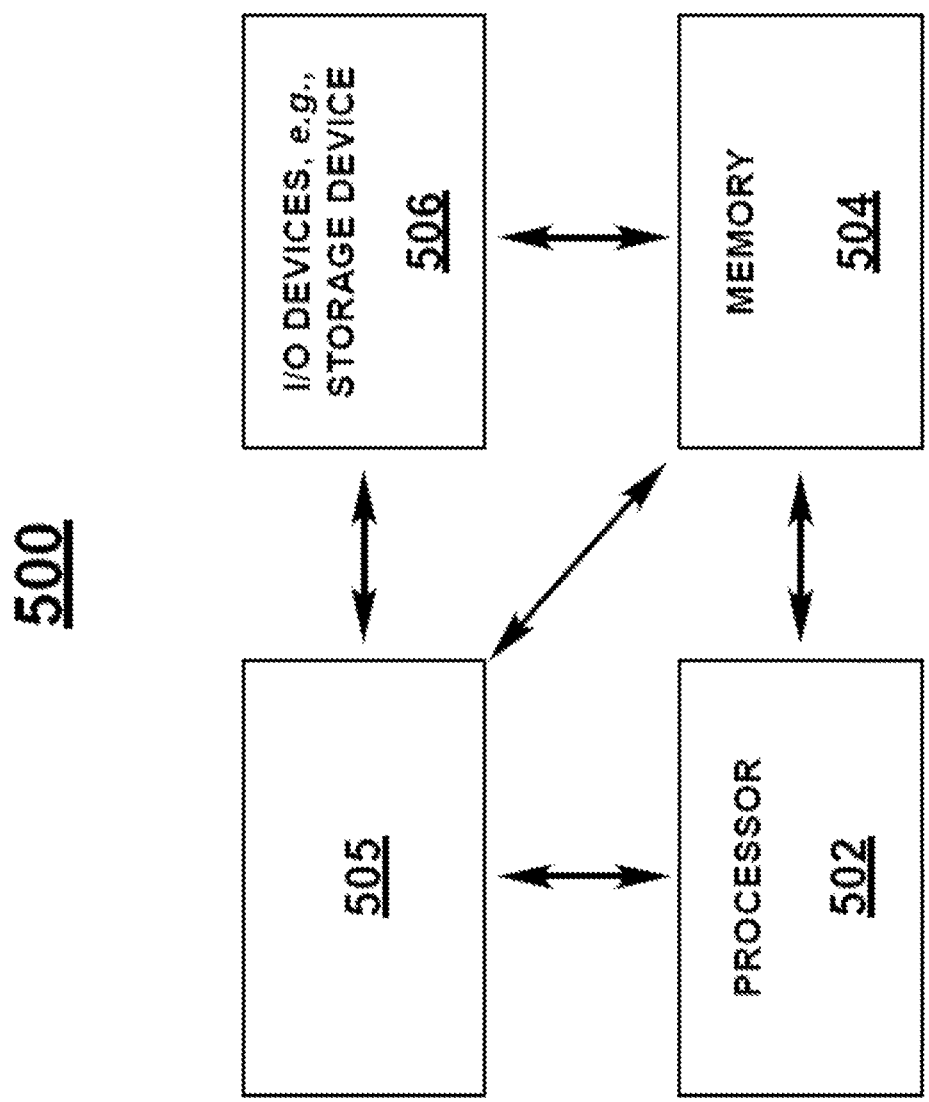

MEAN DNA COPY NUMBER OF CHROMOSOMAL REGIONS IS OF PROGNOSTIC SIGNIFICANCE IN CANCER

CROSS REFERENCE TO RELATED APPLICATIONS

The presently disclosed subject matter claims the benefit of U.S. Provisional Patent Application Ser. No. 61/284,164, filed Dec. 14, 2009, the disclosure of which is incorporated herein by reference in its entirety.

TECHNICAL FIELD

The presently disclosed subject matter relates generally to methods and tests for analyzing recurrent DNA copy number changes in tumor tissue samples from cancer subjects. Copy number is predictive of response to therapy, time of first remission, and in some cases overall survival.

BACKGROUND

It is estimated that there over 4,000,000 cases of canine cancer diagnosed in the United States of America each year, of which up to one quarter are represented by canine lymphoma. While the total number of dogs that are treated for lymphoma is not clear, a conservative estimate is that in the United States of America alone approximately 7,000-10,000 dogs per year are treated with chemotherapy (typically using protocols that include doxorubicin) for lymphoma. The typical cost of this treatment is about $4,000-6,000, resulting in an annual treatment cost in the USA of approximately $30,000,000-$60,000,000.

The vast majority of owners do not treat their dogs for their lymphoma, however. Discussions with veterinary oncologists suggest that one reason for this is the cost of treatment, while another common reason is the "cost versus unknown outcome". A widely used treatment protocol termed "UW-25" is reported to provide up to 90% chance of remission for a median survival of nine months. However, individual remissions can vary from weeks to years, and as a result, the availability of a test that can more accurately predict the duration of remission following therapy would be of great value to clinicians and clients in the decision process.

If such a predictive test were available, many more owners might consider treating their dog for lymphoma, particularly if they were given an accurate predictor of how their dog will respond to therapy, assuming that such a test could be offered at an affordable level of expense. While some owners still would not be in a position to afford the cost of chemotherapy, regardless of possible outcome, there is likely a large number who would be more willing to treat their dogs if they knew that the chance of their pet surviving for, For example, at least a year, was 90-95% or greater. On this basis, the number of candidates that could be considered as a potential beneficiary of a test that would predict time to remission might be substantially higher than 10,000 per year.

Lymphoma is the most common life-threatening cancer in dogs, accounting for up to 24% of all canine malignancies and over 80% of all canine hematopoietic cancers. As in humans, canine lymphoma is a spontaneous malignancy and is generally a disease of middle-aged to older dogs that affects a wide range of breeds.

Untreated cases of canine lymphoma rarely survive beyond three months post-diagnosis, but a large proportion (up to 90%) of canine lymphomas are generally responsive to standards of care using either single agent or multi-agent chemotherapy, increasing both the length and quality of an affected dog's life. Among treated cases receiving the same initial diagnosis, however, there is considerable variation in the extent of response to therapy and overall survival time. This indicates that there is a need to develop more refined modes of classification that are of prognostic significance. At the present time, however, there is no available approach to accurately predict response to chemotherapy of dogs diagnosed with lymphoma.

The PATHVYSION™ HER-2 DNA Probe Kit (Abbott Laboratories, Des Plaines, Ill., United States of America) is designed to detect amplification of the HER-2/neu gene via fluorescence in situ hybridization (FISH) in formalin-fixed, paraffin-embedded human breast cancer tissue specimens. The kit uses the relative copy number of the HER-2 gene to help predict time to remission of the breast cancer.

Described herein is a novel test has been developed for a cancer. The test provides clinicians with the ability to predict with a degree of statistical probability how long before their lymphoma patients will likely enter first remission when treated with a standard of care therapy. There is immediate significance to the veterinary market and predictive potential of the chromosomal regions defined in canine lymphoma in human cancer patients. These regions can inform human oncologists of the likely remission period for human cancer patients.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides in some embodiments methods for predicting the disease free time interval for cancer patients, under consideration for initial or further chemotherapy treatment. In some embodiments, the methods comprise obtaining a biological sample from a patient and detecting the copy number of chromosome region A1 as defined herein. The biological sample can contain a number of cells (i.e. one or more cells). A mean copy number value of chromosome region A1 is in some embodiments determined by dividing the total copy number by the number of cells in the sample. The mean copy number is then correlated with time of first remission.

In some embodiments, the methods include embodiments wherein the patient has lymphoma, such as but not limited to non-Hodgkin's lymphoma.

In some embodiments, the patient is a canine.

The presently claimed subject matter also provides in some embodiments methods wherein the biological sample comprises a biopsy from a patient. The biopsy can be taken from any tissue desired and can comprise tumor and/or lymph node cells.

The presently disclosed methods include embodiments wherein the detecting a copy number of chromosome region A1 comprises contacting the sample with a probe able to detect the presence of chromosome region A1 under conditions sufficient to enable hybridization of the probe to chromosome region A1. The probe can be fluorescently labeled.

In some embodiments, the contacting the biological sample can comprise fluorescence in situ hybridization (FISH) analysis. In some embodiments, the contacting the sample can comprise polymerase chain reaction (PCR) analysis.

In some embodiments, the methods comprise determining the disease free interval (DFI) by substituting the mean copy number of chromosome region A1 per cell value into Formula A, wherein Formula A is:

DFI=374.1685×(mean copy number value for $A1$)−
438.7572 days

In some embodiments, the methods further comprise, before making the risk correlation, detecting the copy number of chromosome region C2. A mean copy number value of chromosome region C2 is in some embodiments determined by dividing the total copy number of chromosome region C2 by the number of cells in the sample. The detecting the copy number of chromosome region C2 can comprise contacting the sample with a probe able to detect the presence of chromosome region C2 under conditions sufficient to enable hybridization of the probe to chromosome region C2.

In some embodiments, the methods further comprise determining the disease free interval (DFI) by substituting the mean copy number of chromosome region A1 and the mean copy number of chromosome region C2 values into Formula AC, wherein Formula AC is:

DFI=367.5094×(mean copy number value for $A1$)+
228.2709×(mean copy number value for $C2$)−
839.22 days In some embodiments, there is a positive correlation between mean copy number of chromosome regions A1 and C2 and duration of disease free time interval.

The presently disclosed subject matter also provides in some embodiments testing kits for predicting disease free time interval in a patient under consideration for initial or further chemotherapy treatment. The kit comprises in some embodiments a probe able to detect the chromosome region A1.

In some embodiments, the testing kits further comprises a probe able to detect chromosome region C2.

In some embodiments, a computer readable medium is provided which has stored thereon computer executable instructions that when executed by a processor of a computer control the computer to perform steps comprising analyzing a mean copy number from chromosome region A1 and/or chromosome region C2 from a biological sample and outputting a predicted DFI. The processor of the computer can employ Formula I and/or II to compute DFI.

It is thus an object of the presently disclosed subject matter to provide methods for predicting the duration of first remission for cancer patients under consideration for initial or further chemotherapy, including chemotherapy comprising doxorubicin or further comprising asparaginase.

An object of the presently disclosed subject matter having been stated hereinabove, and which is achieved in whole or in part by the presently disclosed subject matter, other objects will become evident as the description proceeds when taken in connection with the accompanying drawings and non-limiting examples as best described herein below.

BRIEF DESCRIPTION OF THE DRAWINGS

FIG. 15 is a block diagram of a computer, including a prediction of DFI module (505), suitable for use in performing the functions described herein.

DETAILED DESCRIPTION

I. Definitions

Figure 1:
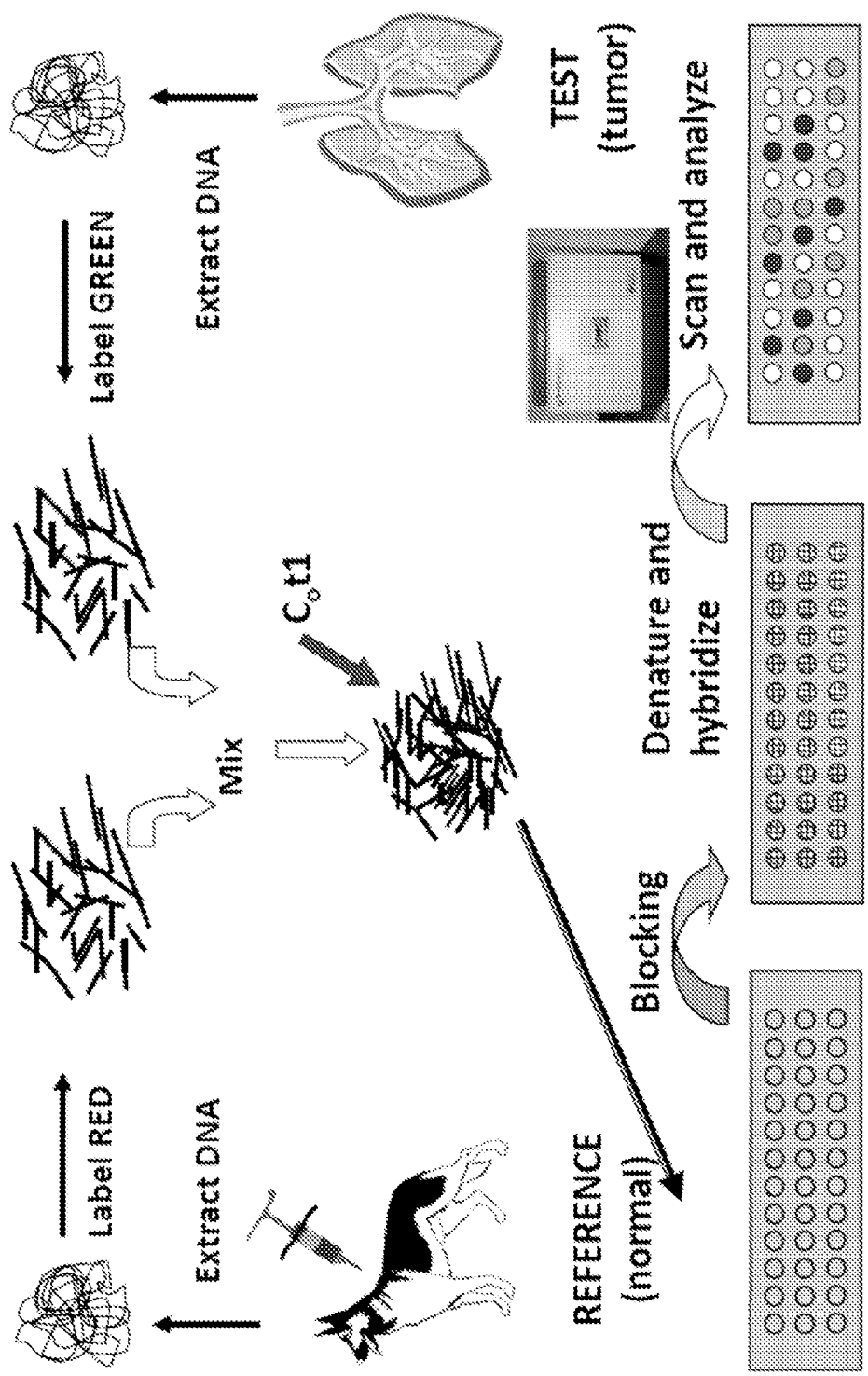
FIG. 1 is a diagram of an exemplary protocol that can be employed for performing comparative genome hybridization (CGH) analysis on an array.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

All references listed herein, including but not limited to patents, patent application publications, journal articles, and database entries (e.g., GENBANK® database entries including all annotations and references cited therein) are incorporated herein by reference to the extent that they supplement, explain, provide a background for, or teach methodology, techniques, and/or compositions employed herein.

Following long-standing patent law convention, the terms "a", "an", and "the" mean "one or more" when used in this application, including the claims. Thus, the phrase "a cell" refers to one or more cells, unless the context clearly indicates otherwise.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, and/or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, the presently disclosed subject matter in some embodiments can "consist essentially of" determining a copy number of a chromosome region in cells obtained from a subject, which means that the recited chromosome region i the only chromosome region for which a copy number is determined. It is noted, however, that a copy number for various positive and/or negative control chromosome regions can also be determined, for example, to standardize and/or normalize the copy number of the selected chromosome region (if desired).

With respect to the terms "comprising", "consisting essentially of", and "consisting of", where one of these three terms is used herein, the presently disclosed and claimed subject matter can include the use of either of the other two terms. For example, the presently disclosed subject matter relates in some embodiments to methods that comprise determining a copy number of a chromosome region identified herein as A1. It is understood that the presently disclosed subject matter thus also encompasses methods that consisten essentially of determining a copy number of a chromosome region identified herein as A; as well as methods that consist of determining a copy number of a chromosome region identified herein as A1.

The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichythyes (bony fish), Amphibia (amphibians), Reptilia (reptiles), Ayes (birds), and Mammalia (mammals)), and all Orders and Families encompassed therein. In some embodiments, the presently disclosed subject matter relates to canine subjects. In some embodiments, the presently disclosed subject matter relates to human subjects.

Similarly, all genes, gene names, and gene products disclosed herein are intended to correspond to orthologs from any species for which the compositions and methods disclosed herein are applicable. Thus, the terms include, but are not limited to genes and gene products from canines and/or humans. It is understood that when a gene or gene product from a particular species is disclosed, this disclosure is intended to be exemplary only, and is not to be interpreted as a limitation unless the context in which it appears clearly indicates. Thus, for example, the genes and/or gene products disclosed herein are also intended to encompass homologous genes and gene products from other animals including, but not limited to other mammals, fish, amphibians, reptiles, and birds.

The various embodiments of the presently disclosed subject matter are particularly useful for warm-blooded vertebrates. Thus, the presently disclosed subject matter concerns mammals and birds. More particularly provided is the use of the methods and compositions of the presently disclosed subject matter on mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the application of the methods and compositions of the presently disclosed subject matter to livestock, including but not limited to domesticated swine (pigs and hogs), ruminants, horses, poultry, and the like.

The term "about", as used herein when referring to a measurable value such as an amount of weight, time, dose, etc., is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods and/or to employ the presently disclosed arrays.

The term "isolated", as used in the context of a nucleic acid or polypeptide (including, for example, a nucleotide sequence, a polypeptide, and/or a peptide), indicates that the nucleic acid or polypeptide exists apart from its native environment. An isolated nucleic acid or polypeptide can exist in a purified form or can exist in a non-native environment.

Further, as used for example in the context of a cell, nucleic acid, polypeptide, or peptide, the term "isolated" indicates that the cell, nucleic acid, polypeptide, or peptide exists apart from its native environment. In some embodiments, "isolated" refers to a physical isolation, meaning that the cell, nucleic acid, polypeptide, or peptide has been removed from its native environment (e.g., from a subject).

The terms "nucleic acid molecule" and "nucleic acid" refer to deoxyribonucleotides, ribonucleotides, and polymers thereof, in single-stranded or double-stranded form. Unless specifically limited, the term encompasses nucleic acids containing known analogues of natural nucleotides that have similar properties as the reference natural nucleic acid. The terms "nucleic acid molecule" and "nucleic acid" can also be used in place of "gene", "cDNA", and "mRNA". Nucleic acids can be synthesized, or can be derived from any biological source, including any organism.

As used herein, the terms "peptide" and "polypeptide" refer to polymers of at least two amino acids linked by peptide bonds. Typically, "peptides" are shorter than "polypeptides", but unless the context specifically requires, these terms are used interchangeably herein.

As used herein, a cell, nucleic acid, or peptide exists in a "purified form" when it has been isolated away from some, most, or all components that are present in its native environment, but also when the proportion of that cell, nucleic acid, or peptide in a preparation is greater than would be found in its native environment. As such, "purified" can refer to cells, nucleic acids, and peptides that are free of all components with which they are naturally found in a subject, or are free from just a proportion thereof.

II. Methods and Compositions for Predicting Disease Free Interval (DFI)

Methods and compositions for predicting the duration of first remission in patients diagnosed with lymphoma are disclosed. It has been discovered that mean DNA copy number of regions on canine chromosomes 1 and 6 within a population of cancer cells are of prognostic significance of disease free time interval in canine lymphoma patients. In some embodiments, the patients received chemotherapy protocols comprising administration of doxorubicin, which in further embodiments was supplemented with L-asparaginase. The methods and compositions are based on nucleic acid technology where nucleic acid probes are hybridized to cell samples and the number of copies of certain genetic regions is quantified. A genetic/cytogenetic test that can offer robust prognostication for canine lymphoma will replace staging in cancer diagnoses.

Within a population of cells isolated from a lymph node biopsy specimen, the mean DNA copy number of selected regions of the canine genome provides statistically significant power to predict disease free interval of canine lymphoma patients treated with chemotherapy that comprises administration of doxorubicin, and which can include L-asparaginase. In this context, disease free interval refers to the time from diagnosis/initial chemotherapy treatment to the time that the patient enters relapse, wherein relapse is a return of the symptoms/signs of cancer after a period of remission. The presently disclosed subject matter has immediate implication for prognostication in veterinary medicine. Use of this test will allow veterinarians to provide a statistical probability of the likelihood of disease free interval in canine patients diagnosed with lymphoma who are treated with standard of care. Further, within a population of cells obtained from human lymphoma specimens, the mean DNA copy number of the corresponding regions of the human genome can similarly be associated with response to therapy for human lymphoma patients.

The presently disclosed subject matter provides methods, kits, and computer readable media for predicting the duration of first remission in patients diagnosed with lymphoma, when treated with a therapy, such as drug therapy, including but not limited to chemotherapy comprising administration of doxorubicin.

In some embodiments, a method for predicting the disease free time interval for a cancer patient under consideration for initial or further treatment comprises obtaining a biological sample from a patient and detecting the mean copy number/cell of chromosome region A1. The patient can be a treated cancer patient or a patient that is being considered for treatment. The sample can be contacted with a probe able to detect the presence of A1 under conditions sufficient to enable hybridization of the probe to A1. The number of copies of A1 is counted and that number is divided by the number of cells in the sample. The sample can contain one or more cells. A positive correlation has been shown between the mean copy number per cell of region A1 and duration of $1^{st}$ remission. In some embodiments a mean copy number greater than two is correlated with an increase in time for DFI.

When the copy number of C2 is added to the model, the prognostic value increases. Again a positive correlation has been shown between the mean copy number per cell of region C2 and duration of $1^{st}$ remission.

The marker A1 was detected by a probe pool of four overlapping canine bacterial artificial chromosome (BAC) clones, which span a 796,156 bp region of dog chromosome 1 (CFA1) between 116,839,835 bp and 117,635,991 bp. The size of the region that presents with abnormal copy number can extend up to the full length of CFA1 (125,616,256 bp). Any marker that hybridizes exclusively to this region of CFA1 or any process that is able accurately to detect copy number of this region can serve as an A1 marker. In addition our data indicate that the full length of CFA1 can be involved and so any marker that hybridizes exclusively to any region of CFA 1 or any process that is able accurately to detect copy number of CFA 1 can serve as an A1 marker.

In the human genome, the region that is evolutionarily conserved with CFA1: 116,839,835-117,635,991 bp resides on human chromosome 19 in band q13.2. This includes the region located at 43,452,745-44,221,900 bp in 19q13.2. These boundaries can move as the genome is refined and so these positions represent the start and end positions of the human chromosome that correspond to the CFA1 regions in the dog.

The marker C2 was detected by a probe pool of five overlapping BAC clones which span an 861,477 bp region of dog chromosome 6 (CFA6) between 41,565,280 bp and 42,426,757 bp. The size of the region that presents with abnormal copy number extends up to the full length of CFA6 (80,642,250 bp). Any marker that hybridizes exclusively to this region of CFA6 or any process that is able accurately to detect copy number of this region can serve as a C2 marker. In addition our data indicate that the full length of CFA6 can be involved and so any marker that hybridizes exclusively to any region of CFA 6 or any process that is able accurately to detect copy number of CFA6 can serve as a C2 marker.

In the human genome, the region that is evolutionarily conserved with CFA6: nucleotides 41,565,280-42,426,757 resides on human chromosome 16 in band p13.1. This includes the region located at nucleotides 1,629,295-2,350,975 in HSA 16p13.1. These boundaries can move as the genome is refined and so these positions represent the start and end positions of the human chromosome that correspond to the CFA 6 regions in the dog. The disease free interval can be predicted by any suitable approach based on the copy number of A1 and/or C2, such as but not limited to employing the representative formulas below using the one variable, A1, Formula A model or the two variable, A1 and C2, Formula AC model.

$$DFI = 374.1685 \times (\text{mean copy number value for } A1) - 438.7572 \text{ days} \quad \text{Formula A}$$

$$DFI = 367.5094 \times (\text{mean copy number value for } A1) + 228.2709 \times (\text{mean copy number value for } C2) - 839.22 \text{ days} \quad \text{Formula AC}$$

The presently disclosed subject matter includes methods wherein the biological sample can comprise tumor cells and/or lymph node cells from a patient, such as might be isolated by a biopsy. The patient can be a dog. The methods include embodiments wherein the patient has been diagnosed with lymphoma, including non-Hodgkin's lymphoma. The patient can be treated or can be proposed for treatment with any therapy, such as chemotherapy including but not limited to chemotherapy comprising administration of doxorubicin and/or L-asparaginase.

The methods and kits provided in accordance with the presently disclosed subject matter can comprise employing one or more DNA probes that are fluorescently labeled to detect the presence of chromosomal regions. The contacting of the biological sample from a patient with the probe(s) can comprise, for example, fluorescence in situ hybridization (FISH) or polymerase chain reaction (PCR). Königshoff et al. (Clinical Chem 49(2): 219-229 (2003)) describe methods of quantification of copy number using Real-Time PCR in a study of HER-2/neu in breast cancer tissue.

The presently disclosed subject matter also provides a testing kit for predicting disease free time interval in a patient treated or proposed for treatment with any therapy, such as chemotherapy including but not limited to chemotherapy comprising administration of doxorubicin and/or L-asparaginase. In some embodiments, the kit comprises a probe(s) able to detect the chromosome regions A1, C2, and/or A1 and C2.

In some embodiments a testing kit is based on assessing mean DNA copy number for chromosome regions A1, C2, and/or A1 and C2 using fluorescence in situ hybridization (FISH) analysis of cells derived from lymph node specimens. Formulas A and/or AC can be employed to predict DFI, as non-limiting examples.

III. Comparative Genomic Hybridization (CGH) Analysis

Comparative genomic hybridization (CGH) is a technique by which differences in copy number of various genomic loci between two sets of samples (e.g., a normal tissue sample and a tissue sample comprising cancer cells) can be determined (see Kallioniemi et al. (1992) Comparative Genomic Hybridization for Molecular Cytogenetic Analysis of Solid Tumors, *Science* 258:818-821; Kallioniemi et al. (1994) Detection and mapping of amplified DNA sequences in breast cancer by comparative genomic hybridization, *Proc Nat Aced Sci USA* 91:2156-2160). A basic strategy for CGH analysis is depicted in FIG. 1. In CGH, DNA from a first tissue (i.e., a tumor or other cancer) and from a second tissue (e.g., normal tissue from the same species or individual) are labeled with different detectable moieties (e.g., fluorescent labels). After mixing the first and second DNA samples with unlabeled $C_0t1$ DNA DNA that has been enriched in repetitive DNA, typically from the same species as from which the first and second DNA samples have been isolated), the mixture is hybridized to a solid support (e.g., a microarray) containing defined DNA probes representing chromosome regions for which copy numbers are to be assayed. The fluorescence at the various locations on the solid support are then detected, thereby providing information with respect to the copy numbers of the carious chromosome regions assayed in the first vs. in the second DNA samples.

Cytogenetic changes in a variety of canine cancers were analyzed by developing a custom, genome-wide, assembly integrated canine BAC array (1 megabase (Mb) resolution) for evaluation of recurrent DNA copy number changes. Canine cancer patients were simultaneously recruited and evaluated for clinical follow-up. The approach identified a series of recurrent DNA copy number changes in a variety of canine cancers (e.g., lymphoma, osteosarcoma, intracranial malignancies, soft tissue sarcomas, etc.).

Several of these recurrent changes are evolutionarily conserved with the corresponding human cancer. Gene discovery, treatment, and prognosis in the dog can thus be translate to corresponding human cancers.

Using the treatment regime and clinical outcome permitted identification of associations between cytogenetic changes and response to therapy (time of first remission, overall survival).

Recurrent DNA copy number aberrations (CNAs) were identified in canine lymphoma, including copy number changes of regions of several dog chromosomes including chromosomes 1, 6, 11, 13, 14, 16, 18, 31, 37 and 38. These are the ten (10) probes referred to in Example 2 herein below. The influences of these DNA CNAs were tested by looking at their presences in a panel of canine lymphoma patients with known outcomes following treatments with standard of care chemotherapy. Tissue samples from a study population were obtained from Colorado State University (CSU), Fort Collins, Colo., United States of America. The population included 322 lymph node biopsy specimens. These specimens had been obtained from a series of canine patients that were recruited as part of multicenter clinical trial. In the clinical trial, each of the dogs had received single agent (doxorubicin) chemotherapy (supplemented with L-asparaginase) and then those dogs in remission at 15 weeks into treatment (n=250) were further treated with either a "test" compound (n=125) or placebo (n=125) as part of a double blind placebo controlled trial (described below).

Comparative genomic hybridization is a molecular cytogenetic technique that allows evaluation of DNA copy number changes on a genome-wide level. Two custom BAC arrays were developed by selecting clones spaced every 10 Mb and then every 1 Mb throughout the genome of the dog. Use of these arrays provided for the evaluation of a large number of canine tumor DNA samples and for the identification of regions of the genome that were commonly altered in DNA copy number.

Cytogenetic evaluation (comparative genomic hybridization) of a small number (n=25) of canine lymphomas identified a series of 10 recurrent DNA copy number changes. These changes remained evident when the number of cases reached over 100, thus these 10 regions were selected for their roles in prognosis of survival.

Figure 2:
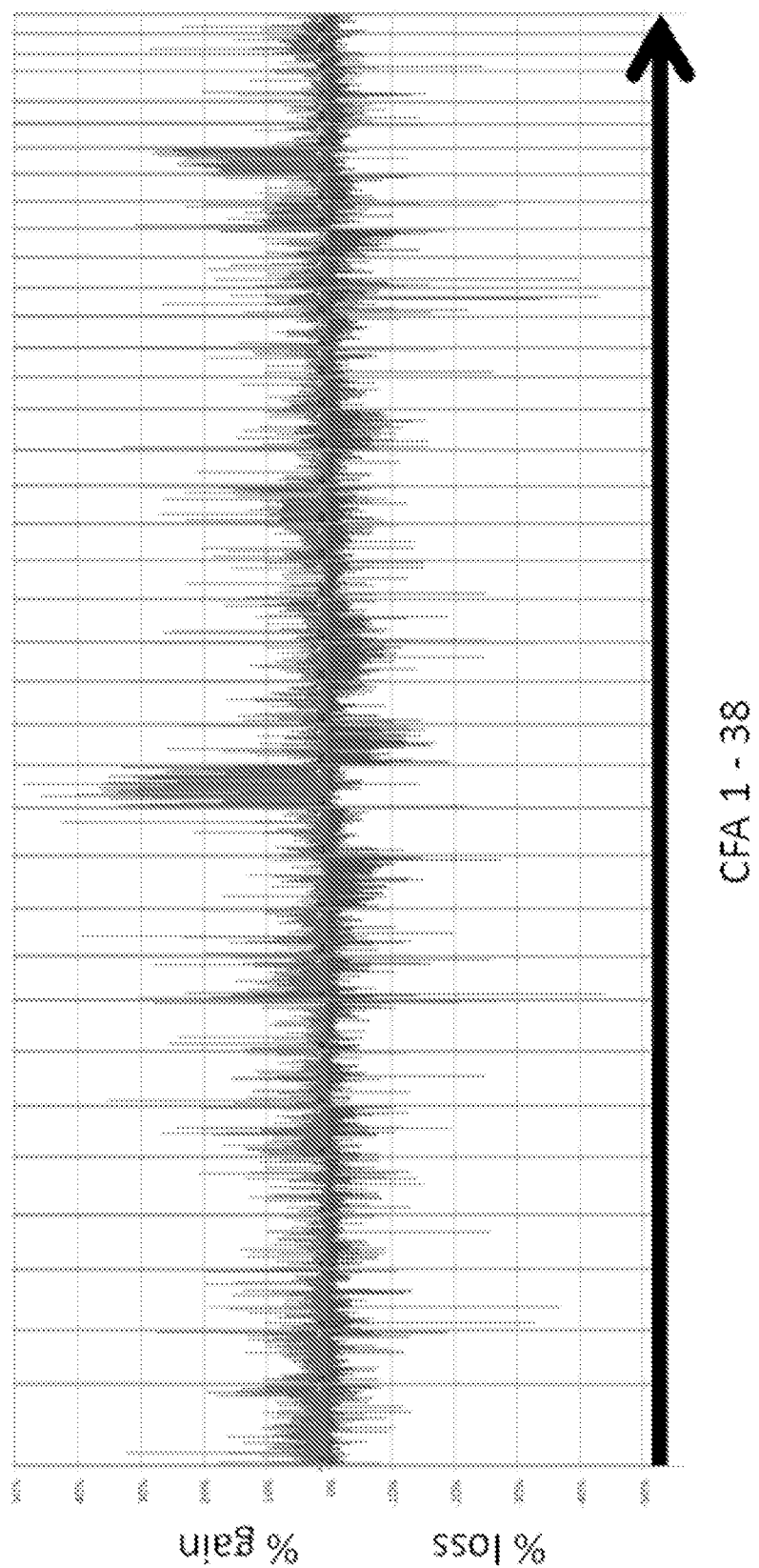
FIG. 2 is a graph depicting the frequency of DNA copy number increases (gain) and decreases (loss) observed across a collection of over 200 cases of canine lymphoma. The x-axis represents positions along the 38 pairs of autosomes in the canine genome (CFA1-38).

The most frequent whole chromosome copy number changes in canine lymphoma are gains of dog chromosomes 13 and 31. See FIG. 2. In addition there are numerous smaller regions of gain and loss throughout the genome. These smaller regions were assessed also to determine which were associated with prognosis.

The findings from the canine work are simultaneously translated to corresponding regions of the human genome to investigate whether data from studies of the dog can benefit prognostic advances in human cancers.

IV. Computer Readable Storage Media

The presently disclosed subject matter also provides in some embodiments computer readable storage media such that the presently disclosed models (including, but not limited to Formulae A and AC) can be executed in a computer program. Thus, in some embodiments, the subject matter described herein for predicting DFI can be implemented in hardware, software, firmware, or any combination thereof. As such, the terms "function" or "module" as used herein refer to hardware, software, and/or firmware for implementing the feature being described.

Thus, in some embodiments the subject matter described herein for predicting DFI can be implemented using a computer readable storage medium having stored thereon executable instructions that when executed by the processor of a computer control the computer to perform steps of analyzing copy number from chromosome region A1, chromosome region C2, and/or chromosome regions A1 and C2, from a biological sample and outputting a predicted DFI. The processor provided in the computer readable medium can employ Formula A and/or Formula AC to compute DFI, as non-limiting examples.

FIG. 15 is a block diagram of a computer suitable for use in performing the functions described herein. As depicted in FIG. 15, a system 500 comprises a processor element 502 (e.g., a CPU), a memory 504, e.g., random access memory (RAM) and/or read only memory (ROM), a prediction of DFI module 505, and various input/output devices 506 (e.g., storage devices, including but not limited to, a tape drive, a floppy drive, a hard disk drive or a compact disk drive, a receiver, a transmitter, a speaker, a display, a speech synthesizer, an output port, and a user input device (such as but not limited to a keyboard, a keypad, a mouse, and the like)).

It should be noted that the presently disclosed subject matter can be implemented in software and/or in a combination of software and hardware, e.g., using application specific integrated circuits (ASIC), a general purpose computer or any other hardware equivalents. In one embodiment, the present prediction of DFI module or process 505 can be loaded into memory 504 and executed by processor 502 to implement the functions as discussed above. As such, the present prediction of DFI process 505 (including associated data structures) of the presently disclosed subject matter can be stored on a computer readable medium or carrier, e.g., RAM memory, magnetic or optical drive or diskette and the like.

Exemplary computer readable storage media suitable for implementing the subject matter described herein includes disk memory devices, chip memory devices, programmable logic devices, and application specific integrated circuits. In some implementations, the computer readable storage medium can include a memory accessible by a processor of a computer or other like device. The memory can include instructions executable by the processor for implementing any of the methods for predicting DFI as described herein. In addition, a computer readable medium that implements the subject matter described herein can be located on a single device or computing platform or can be distributed across multiple physical devices and/or computing platforms.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Clones

Chromosome Region A1.

For assessment of the copy number of the chromosome region designated herein as A1, a probe pool of four BAC clones was used. The four overlapping clones span a 796,156 base pair (bp) region of canine chromosome 1 (CFA1) between nucleotide 116,839,835 and nucleotide 117,635,991 as set forth in the CanFam2 genome assembly (Broad Institute of MIT/Harvard, Cambridge, Mass., United States of America) available from the website of the University of Santa Cruz (Santa Cruz, Calif., United States of America) and also disclosed as nucleotides 116,839,835-117,635,991 of GENBANK® Accession No. NC_006583. Evaluation of cases with copy number changes of chromosome region A1 showed that the actual size of the region that presented with abnormal copy number can extend up to the full length of the chromosome (125,616,256 bp).

In the human genome, the region that is evolutionarily conserved with CFA1 (i.e., nucleotides 116,839,835-117,635,991 of canine chromosome 1; GENBANK® Accession No. NC_006583) resides on human chromosome 19 in band q13.2. This region includes the region located at nucleotides 43,452,745-44,221,900 of human chromosome 19 that includes 19q13.2 (see GENBANK® Accession No. NC_000019). These boundaries can move as the genome is refined and so these positions represent the start and end positions of the human chromosome that correspond to the CFA1 regions in the dog.

Chromosome Region C2.

For assessment of the copy number of the chromosome region designated herein as C2, a probe pool of five BAC clones was used. The five overlapping clones span an 861,477 by region of canine chromosome 6 (CFA6) between nucleotide 41,565,280 and nucleotide 42,426,757 as set forth in the CanFam2 genome assembly (Broad Institute of MIT/Harvard, Cambridge, Mass., United States of America) and also disclosed as nucleotides 41,565,280-42,426,757 of GENBANK® Accession No. NC_006588. This region contains the gene tuberin (TSC2) that maps in the dog at CFA6:41,934,226-41,940,068. As with chromosome region A1, evaluation of cases with copy number changes of chromosome region C2 showed that the size of the region that presented with abnormal copy number extended up to the full length of the chromosome (i.e., 80,642,250 bp).

In the human genome, the region that is evolutionarily conserved with CFA6 (i.e., 41,565,280-42,426,757 of canine chromosome 6; nucleotides 41,565,280-42,426,757 of GENBANK® Accession No. NC_006588) resides on human chromosome 16 in band p13.1. The region includes the region located at nucleotides 1,629,295-2,350,975 by of human chromosome 16 that includes 16p13.1 (see GENBANK® Accession No. NC_000016). These boundaries can move as the genome is refined and so these positions represent the start and end positions of the human chromosome that correspond to the CFA6 regions in the dog. The tuberin gene (TSC2) in human maps to HSA16:2,038,617-2,036,695, and so is within this region.

The BAC clones used specifically for assessing copy number of each region for the development of the presently disclosed subject matter are derived from the CHORI-82 canine BAC library, details of which are available from the website of the Children's Hospital Oakland Research Institute (Oakland, Calif., United States of America; see CHORI-82: Canine Boxer (F) (*Canis familiaris*) BAC Library; library identification number 253) on the World Wide Web. Table 1 and show the start and end positions in the canine genome assembly (CanFam2) for the clones employed herein. In addition to use of these specific canine BAC clones, any genomic DNA that hybridizes effectively and exclusively to the regions defined herein as chromosome regions A1 and C2 can be employed as suitable probes in FISH to implement the presently disclosed subject matter. Further, any process that allows accurate determination of mean copy number of these regions within a population of cells can be used to implement the presently disclosed subject matter, and is thus encompassed by the present disclosure.

TABLE 1

Chromosome Region A1 (CFA 1) Evaluation with Representative, Non-limiting Four BAC Clones

| A1 Clones | Start Position* | End Position* | Length | Overlap | Total length of probe pool |
|---|---|---|---|---|---|
| A | 116839835 | 117080644 | 240810 | 19889 | 796156 |
| B | 117060755 | 117226554 | 165800 | 12993 | |
| C | 117213561 | 117419798 | 206238 | 9618 | |
| D | 117410180 | 117635991 | 225812 | | |

*Start and End Positions refer to nucleotide positions in the CanFam2 genome assembly or GENBANK ® Accession No. NC_006583

TABLE 2

Chromosome Region C2 (CFA 6) Evaluation with Representative, Non-limiting Five BAC Clones

| C2 Clones | Start Position* | End Position* | Length | Overlap | Total length of probe pool |
|---|---|---|---|---|---|
| A | 41565280 | 41750903 | 185624 | 48404 | 861477 |
| B | 41702499 | 41917747 | 215249 | 75322 | |
| C | 41842425 | 42061613 | 219189 | 66636 | |
| D | 41994977 | 42256794 | 261818 | 30789 | |
| E | 42226005 | 42426757 | 200753 | | |

*Start and End Positions refer to nucleotide positions in the CanFam2 genome assembly or GENBANK ® Accession No. NC_006588

Example 2

Canine Lymphoma Treatment Protocol Used for the Patient Population Assessed Patients Canine patients of any breed, weight, and sex were eligible for inclusion. Dogs could not have received any prior chemotherapy. Patients had not received any corticosteroids within the last 30 days prior to staging. Patients did not have concurrent disease that would require therapy (such as diabetes), and had to have a life expectancy of at least one year.

Patients were staged according to the World Health Organization (WHO) criteria for canine lymphoma. Evaluation included complete history and physical exam, CBC, biochemical profile, urinalysis, chest and abdominal radiographs, bone marrow aspirate, and lymph node biopsy (in most cases excisional).

Figure 5:
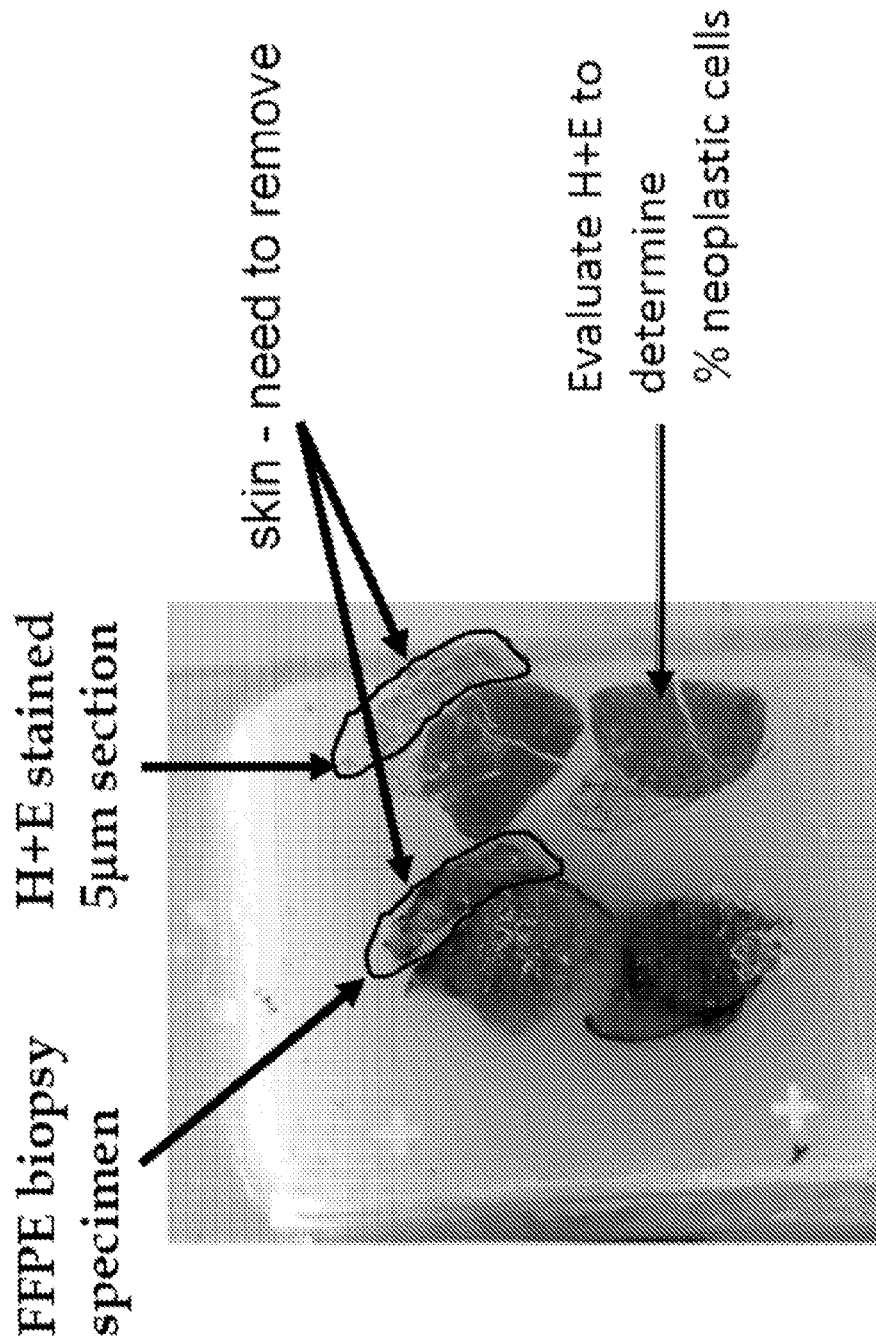
FIG. 5 is an image of biopsied tumor tissue. Cases from the trial disclosed herein were coded and provided in a blind manner. Each of the cases was reviewed to determine the presence of large regions of non-neoplastic tissues (e.g., skin), and these were noted on the hematoxylin and eosin stain (H+E).
Figure 6:
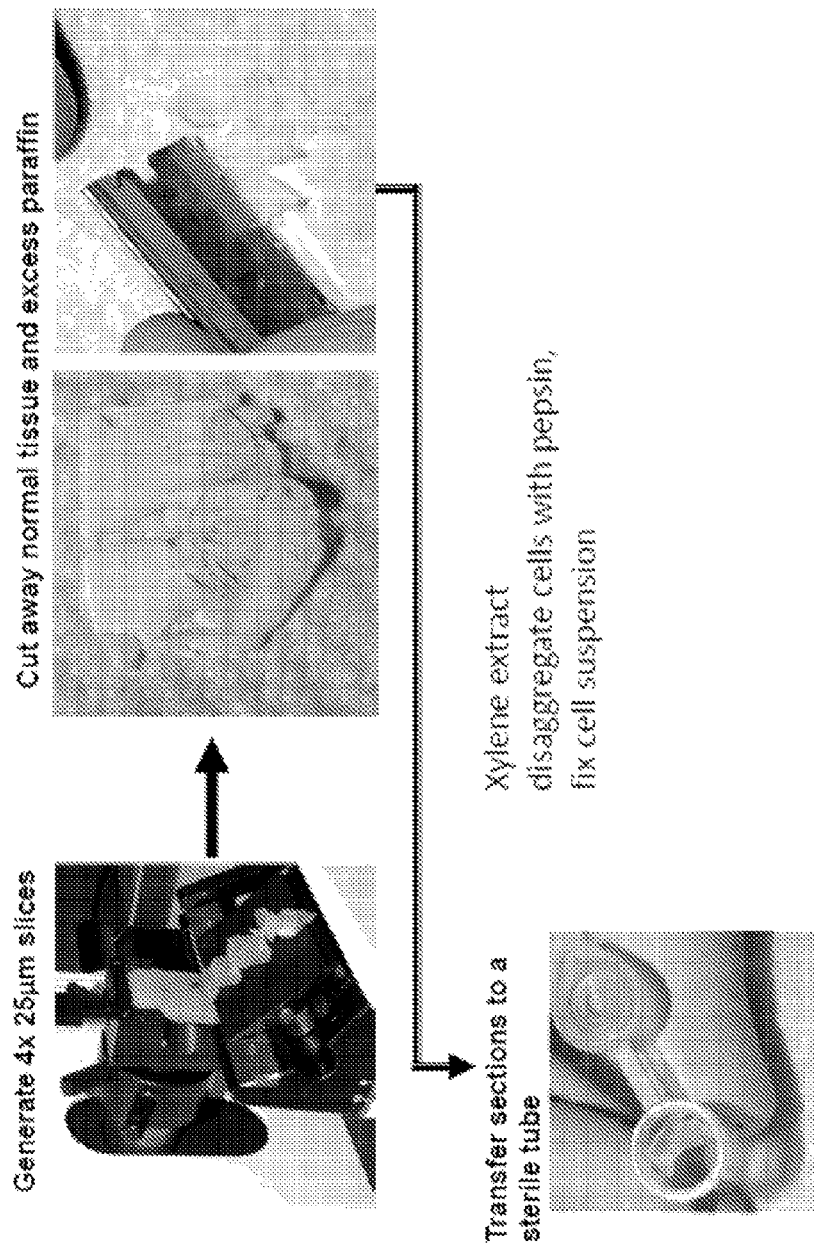
FIG. 6 is a series of images showing an exemplary procedure that can be used for isolation and characterization of tumor cells. To obtain a sufficient number of intact nuclei, 25 micron slices of paraffin-embedded tissue, which are thicker than one cell, can be removed from each tissue block, and any large regions of non-neoplastic tissue can be macro-dissected away. The remainder of the slice can be put into a microfuge tube and the tissue extracted with xylene. Pepsin can be used to generate a cell suspension, which can then be fixed in readiness to make preparations on glass slides.
Figure 7:
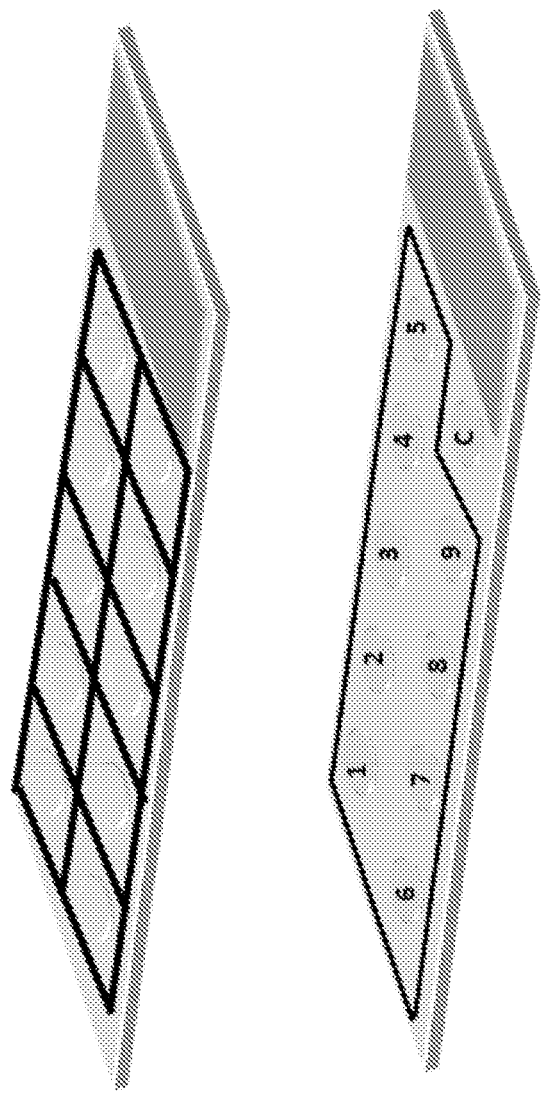
FIG. 7 is a diagram showing an exemplary approach that can be used to assess copy number. Cells from several cases can be applied to a single slide. The slide can be masked with rubber cement to ensure no cross contamination of each individual cell preparation. This approach can allow for a greater level of inter-case consistency and minimized probe variability.
Figure 8:
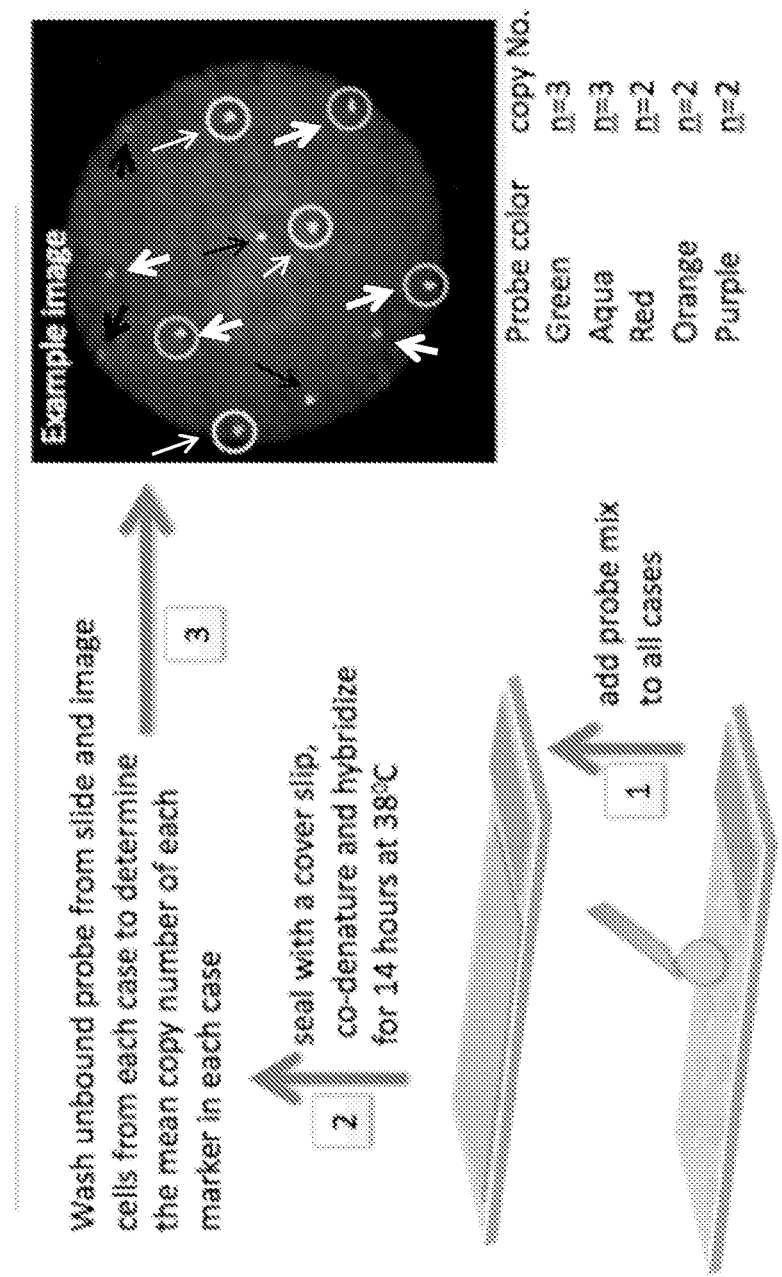
FIG. 8 is a diagram depicting a case of multi-color, multi-case hybridization. The cases on each slide of FIG. 7 were used as templates for multicolor fluorescence in situ hybridization (FISH), where the cells were exposed to a common hybridization mix containing fluorescently labeled DNA representing the regions being evaluated for genomic copy number. The signals generated by the hybridization were then determined using multi-plane fluorescence microscopy, which produced images such as the cell depicted in the top right panel of FIG. 8. This single cell was from a canine lymphoma patient that had been hybridized with five differentially labeled probes. Since the five fluorophores employed were spectrally discrete, they were easy to distinguish as red, orange, green, aqua, and purple spots in the actual photomicrograph. The cell was also counterstained with 4',6-diamidino-2-phenylindole (DAPI), a fluorescent dye that binds to DNA and stains nuclei blue. In a non-neoplastic cell, the copy number of each locus was expected to be n=2. In this lymphoma cell, the copy number of the red (uncircled spots identified by the thick black arrows), orange (uncircled spots identified by the thin black arrows), and purple (uncircled spots identified by the thick white arrows) probes was two, while the green (circled spots identified by the thick white arrows) and aqua (circled spots identified by the thin white arrows) probes both had three copies. These two probes represented regions of canine chromosomes 13 and 31, respectively.
Figure 9:
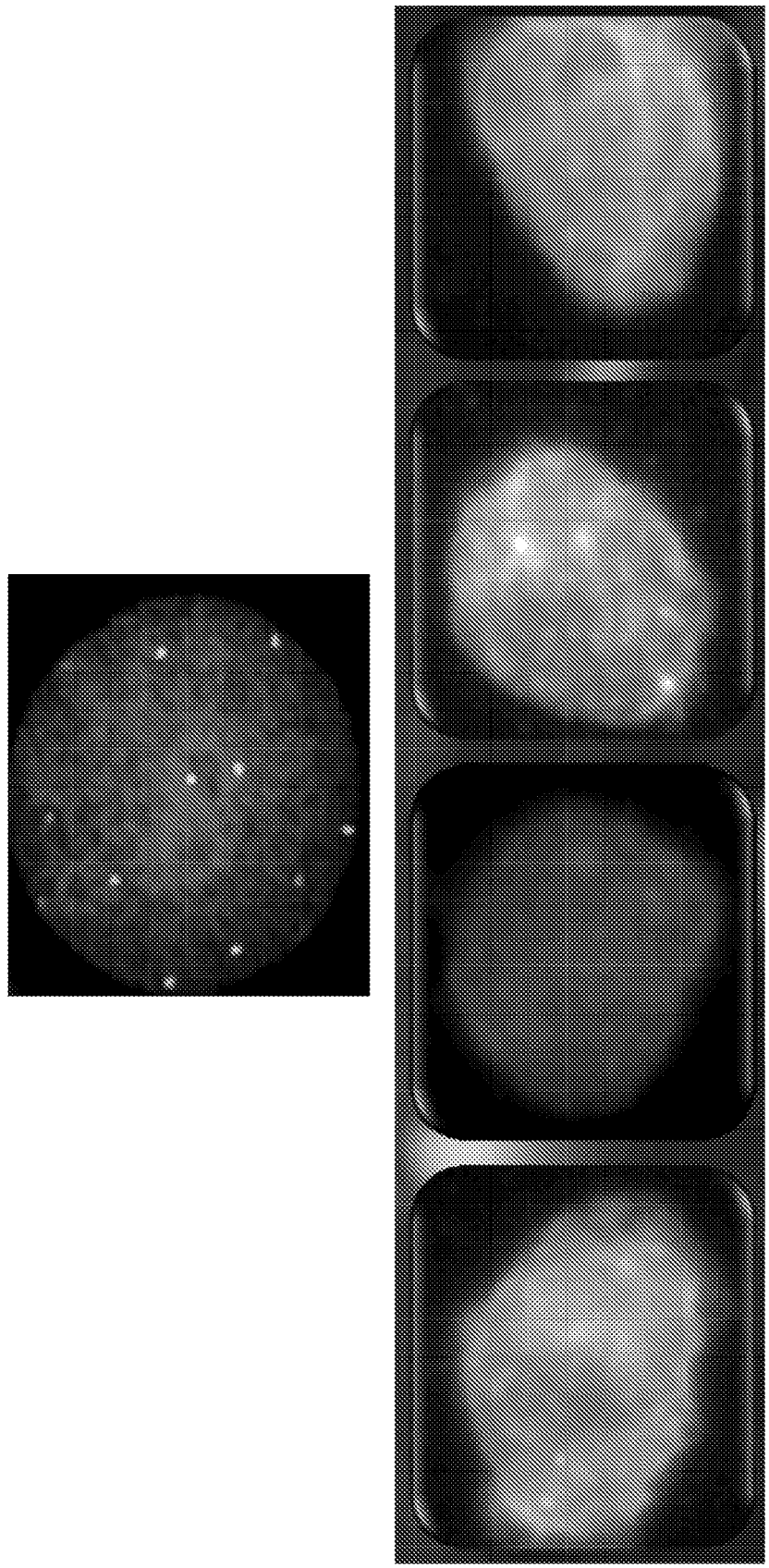
FIG. 9 is a series of images showing the technical challenges that can arise when using archival samples. The cell in the top image was a cell from a fresh lymph node biopsy. Note the sharp dots indicative of detected chromsomoes. The four cells in the bottom images were each single plane images of data obtained from cells isolated from a formalin fixed paraffin block, showing high levels of background fluorescence.

Lymph node biopsies were obtained prior to any treatment (see FIG. 5), fixed in zinc formalin, and embedded in paraffin for routine histology. Only cancer stage 3a and 4a patients were included. The number of patients enrolled was 322.

Treatment.

Patients received doxorubicin at a dose of 30 mg/m$^2$ in 150 cc of a 0.9% NaCl infused intravenously over 20 minutes. Doxorubicin was given every three weeks for a total of five treatments. To enhance remission status, patients also received L-asparaginase weekly for three weeks, with the first dose given 6-24 hours after the first dose of doxorubicin. At the time of the 5$^{th}$ treatment, if the patient was in remission, the patient was randomized to receive either an investigational agent or placebo as part of a double blind placebo controlled trial. The number of patients in remission at the time of the 5$^{th}$ treatment was 250.

Figure 3:
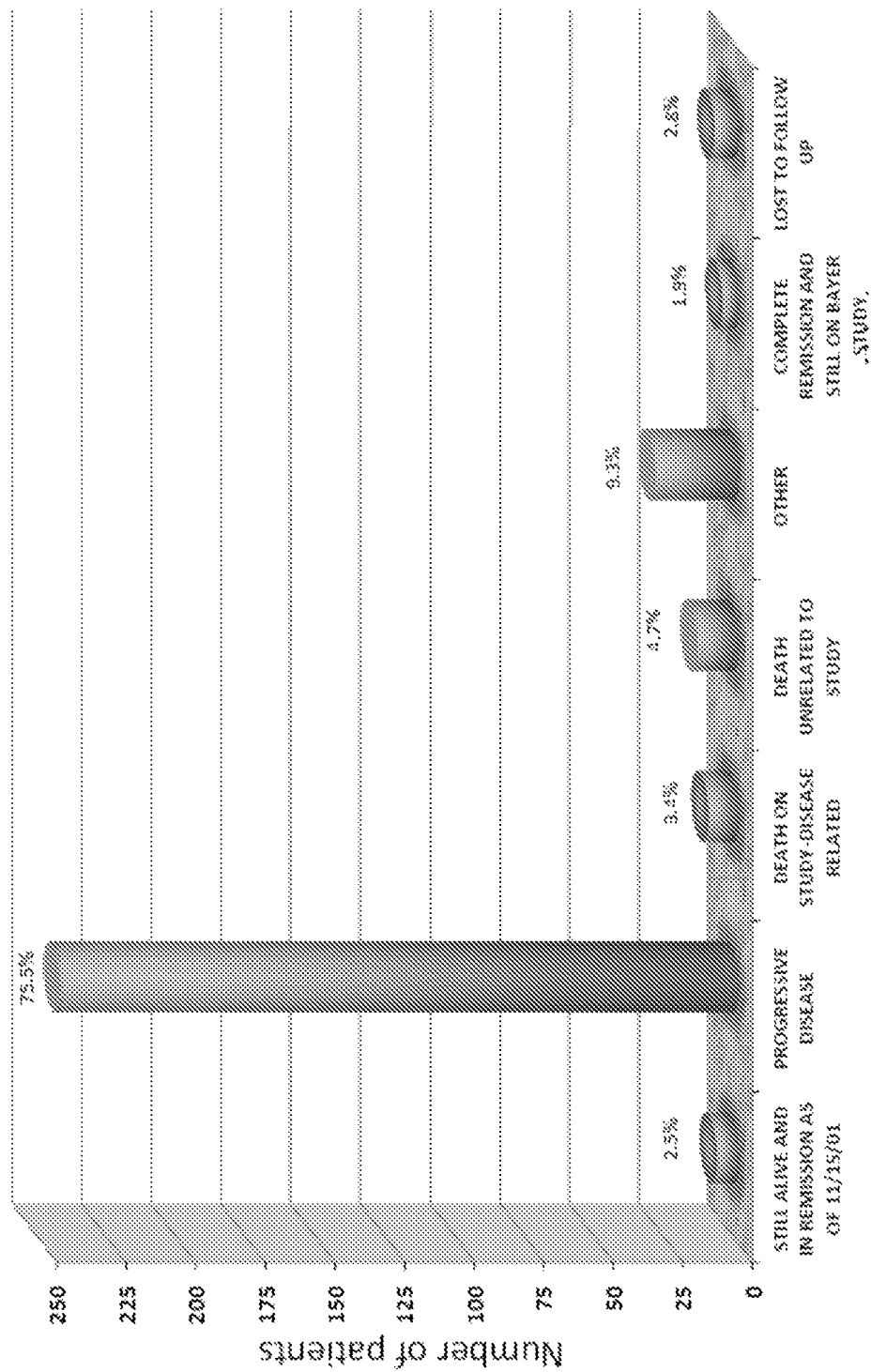
FIG. 3 is a bar graph showing the number and circumstances under which individual patients (n=322) left a study disclosed herein.

Of the patients enrolled, 72 dogs were classified as "early failures". These patients did not make it to investigational drug randomization. See FIG. 3. They "failed" either by coming out of remission before treatment Number 5 or they never went into remission. This group represented dogs that had cancer that did not respond as well as would be predicted.

Patient Follow Up.

The remaining patients were then followed every six weeks to assess remission status until the end of the first remission or up to two years, whichever came first. The follow up evaluation included a physical exam, chest and abdominal radiographs, and blood work (CBC, biochemical profile, urinalysis).

At the end trial, there was no significant difference in the outcome of the two study populations (+/- investigational therapy). Thus, statistically, all dogs had received the same treatment. Detailed signalment, including age, breed, gender, lymphoma subtype, and disease free interval, had been recorded for each patient. For many, the immunophenotype of the lymphoma was also available.

Figure 4:
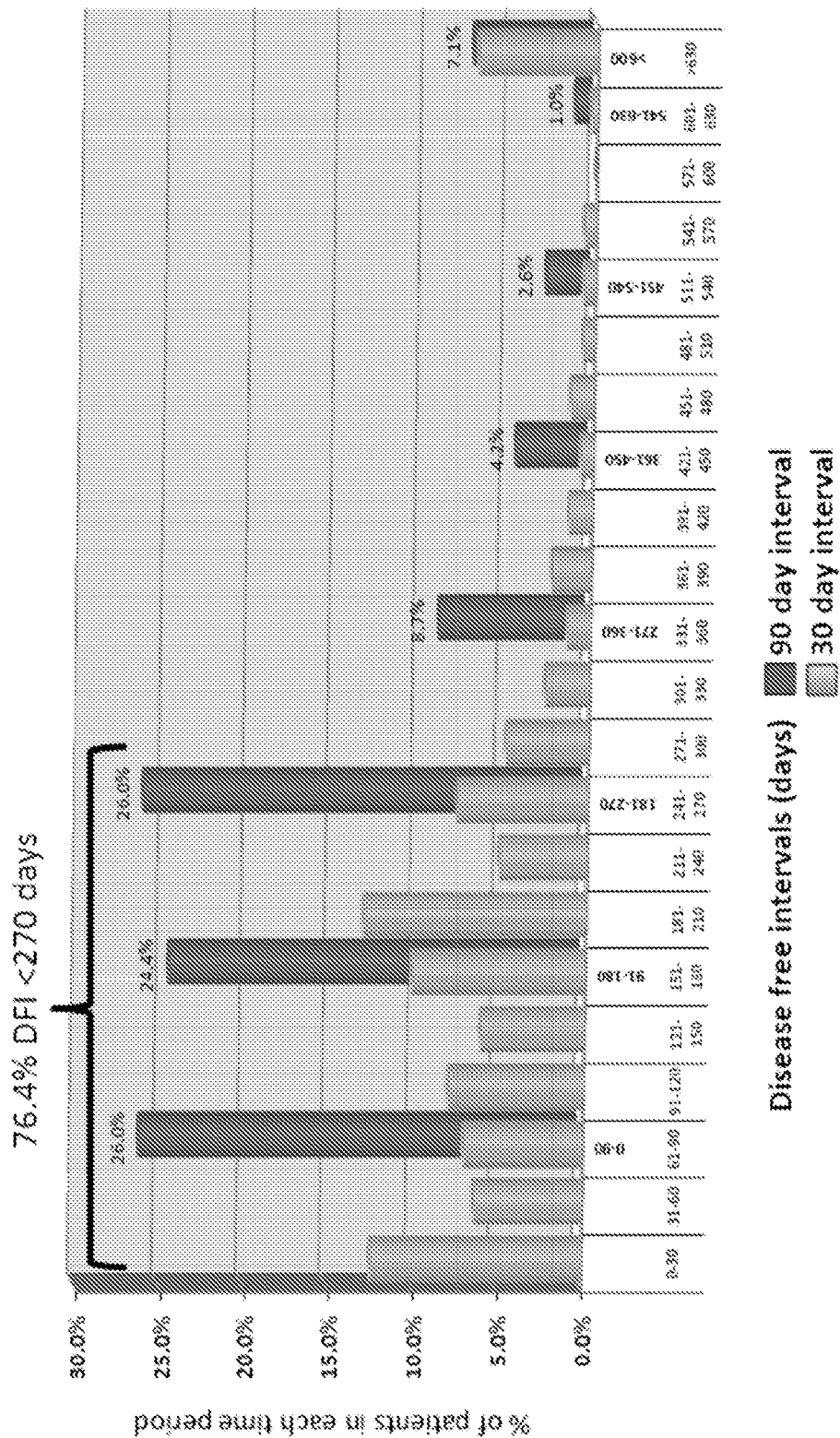
FIG. 4 is a bar graph showing the distribution of the 322 patients with regard to their Disease Free Interval (DFI). Darker bars represent 90 day intervals and lighter bars represent 30 day intervals.

Clinical disease free interval (DFI) was calculated from the time of diagnosis (initial visit) to time of relapse during a scheduled visit. This time period was determined by staging procedures, including history, physical exam, CBC, chemistry panel, chest and abdominal radiographs, and Karnofsky's scores (Karnofsky & Burchanot (1949). *The clinical evaluation of chemotherapeutic agents*. Columbia University Press, New York<N.Y., United States of America). The DFI of each of these patients is summarized in FIG. 4.

Example 3

Scoring Archival Samples

Unlike fresh, unfixed cells, FISH analyses of formalin fixed cells typically presents a set of technical challenges. Factors such as time from surgery to fixation, size of the specimen, fixation parameters and post-fixation storage conditions can all potentially affect the quality of FISH—especially signal to noise ratio. Formalin fixed cells generated much greater background signal, and thus were not easy to interpret. See FIGS. 6-9.

Figure 10A:
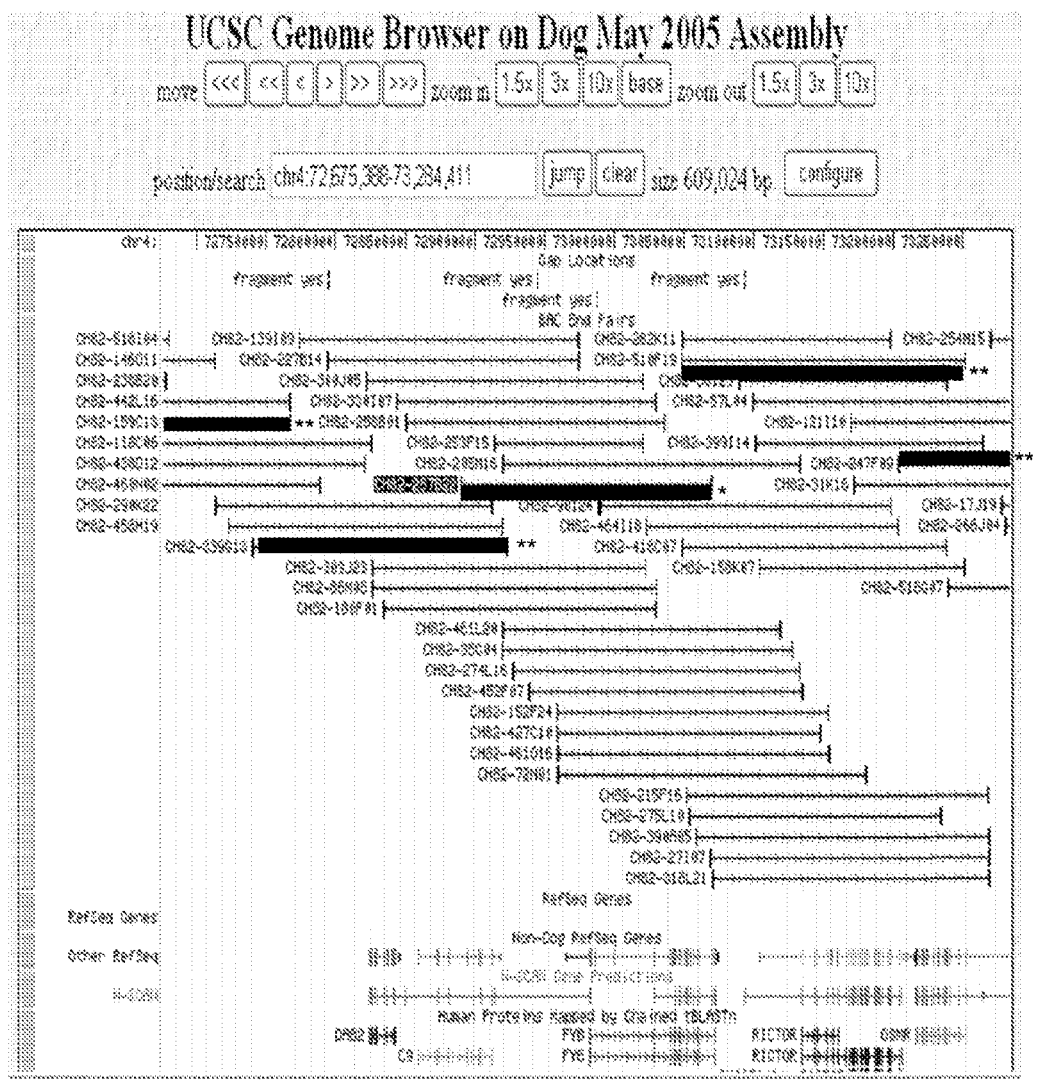
FIGS. 10A-10E shows a diagram and a photomicrograph, respectively, of the development of BAC contigs to increase the signal:noise ratio (FIG. 10A) and improve scoring of BAC clones (FIGS. 10B-10E). The probes used in conventional FISH were generally single BAC clones that each spanned approximately 200 kilobases (kb) of the canine genome (e.g., the thick black line identified with a single asterisk to its right in FIG. 10A). These probes generally provided a small but easily scored signal when used in FISH of non-fixed cells (see FIG. 10B), but produced a high background when used with fixed cells (see FIG. 10D). When overlapping BAC clones were selected (thick lines in FIG. 10A identified with double asterisks) then pooled and labeled with a fluorochrome, the resulting signal was much larger in unfixed cells (compare signal size in FIG. 10C to that in FIG. 10B). In fixed nuclei, this increase in signal size (FIG. 10E) allowed also for reduction in background noise (compare FIG. 10E to FIG. 10D) and permitted scoring with confidence. As with existing cytogenetic testing, there was a small frequency (up to 3%) of "normal" cells, both from fixed or unfixed tissues, that had a copy number of n=1, though the frequency of "normal" cells with n>2 was zero.
Figure 10:
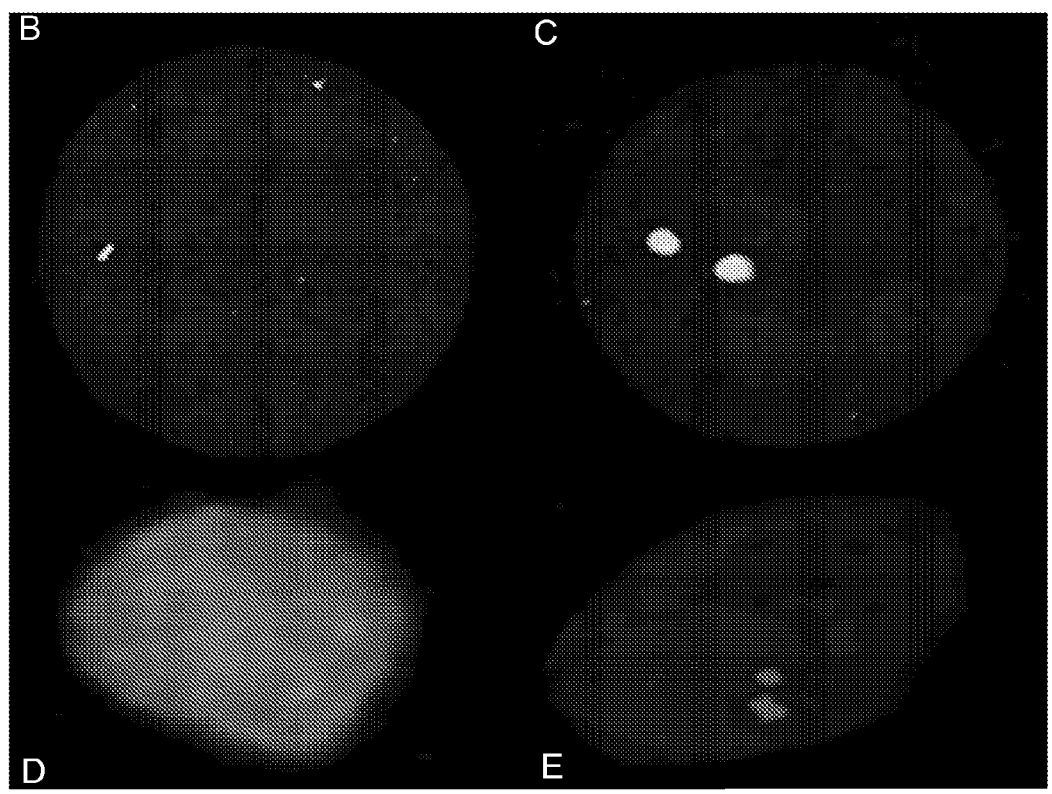

To overcome these issues, a robust protocol that generated higher signal to noise ratio is provided herein. The protocol included modified pretreatment of fixed cells as well as use of longer, contiguous BACs. The use of single BACs as probes in cells derived from fixed tissues generally resulted in weaker signal and with a higher background. See FIGS. 10D and 10E. Referring to FIG. 10, both cells in FIG. 10D and FIG. 10E were fixed, but the cell in FIG. 10E was easy to score compared to the cell in FIG. 10D due to the use of the pool of probe. To overcome the signal to noise ratio issue in fixed cells, a series of overlapping BAC clones were selected from the genome assembly such that the total length of the overlapping probes was approximately 800 kilobases (Kb). See Tables 1 and 2.

Figure 11:
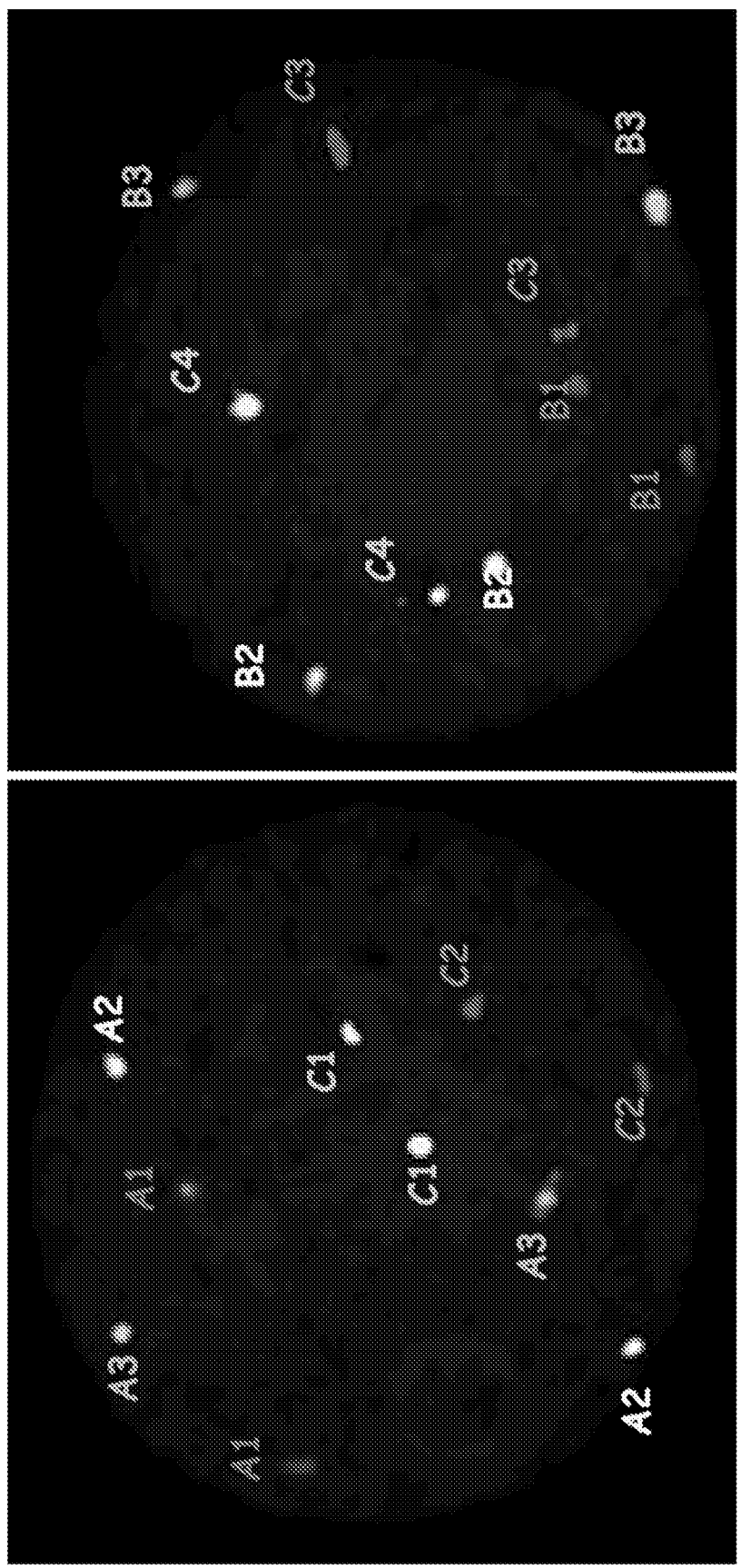
FIG. 11 is an image showing single locus probe (SLP) analysis of 10 probes (in two sets of five probes, one each in the left panel and in the right panel) on unfixed non-neoplastic lymphocytes. No neoplastic cells are shown. The copy number is n=2 for all 10 probe pools.
Figure 12:
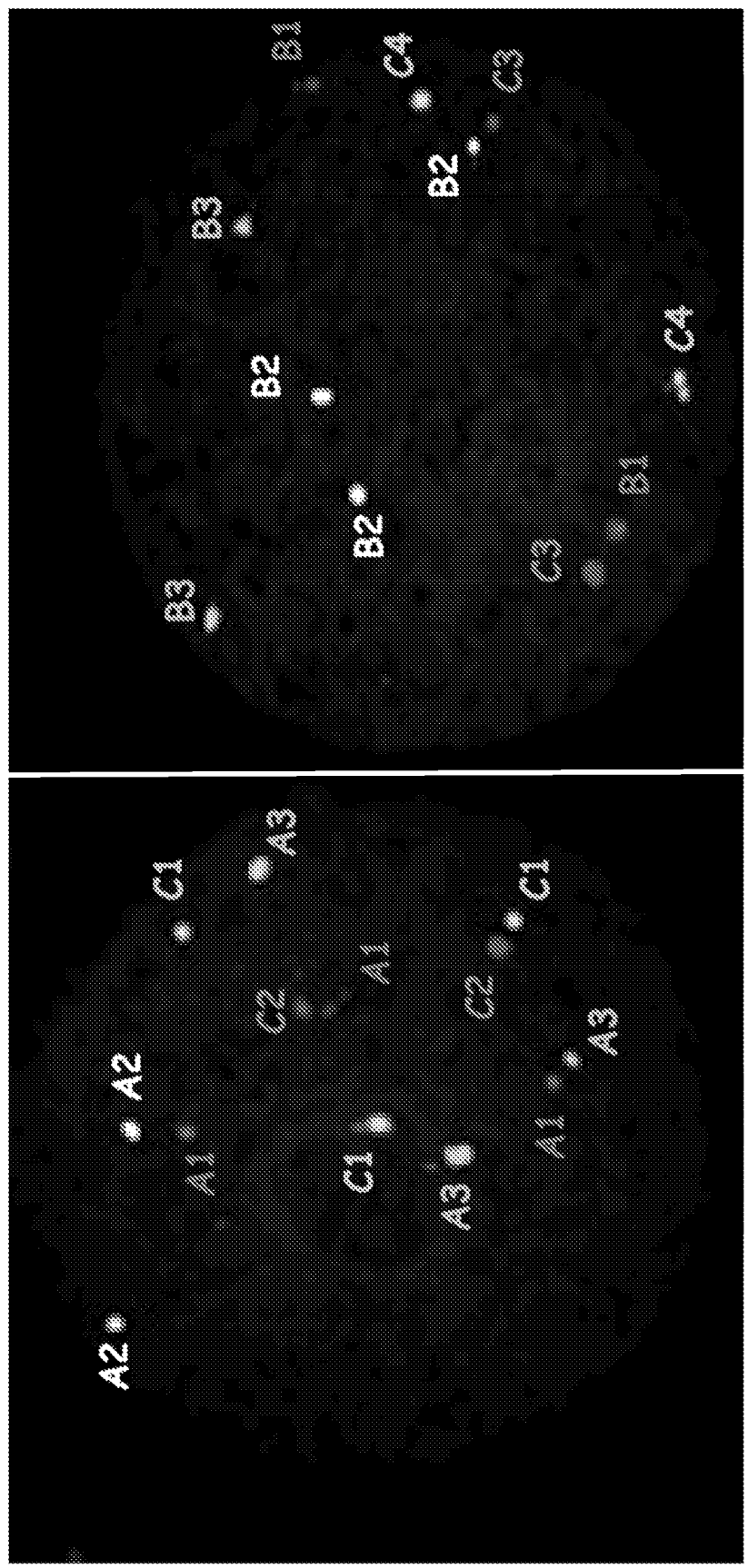
FIG. 12 is an image depicting SLP analyses of the same panel of 10 probes in FISH of unfixed lymphoma cells. In the left panel the copy number of chromosome regions A1, A3, and C1 is n=3, and in the right panel the copy number of B2 is n=3. As with non-neoplastic cells, in unfixed neoplastic cells, these ten loci were routinely evaluated in two reactions, each with five differentially labeled BAC pools.

Ten regions selected for investigation in EXAMPLE 2 were rigorously evaluated in normal unfixed cells to determine probe quality and to evaluate reliability. See FIGS. 11 and 12. As is the case in human studies, there was a small percentage of cells that showed only one copy of the tested locus, perhaps due to spontaneous deletions and/or to the probe being unable to access the site of the second locus within the nucleus. Counts of several hundred "normal" cells did not reveal additional copies of any of the ten loci. Copy number n=1 was seen in up to 3% of cells. Copy number n>2 was seen in 0% of cells.

Figure 13:
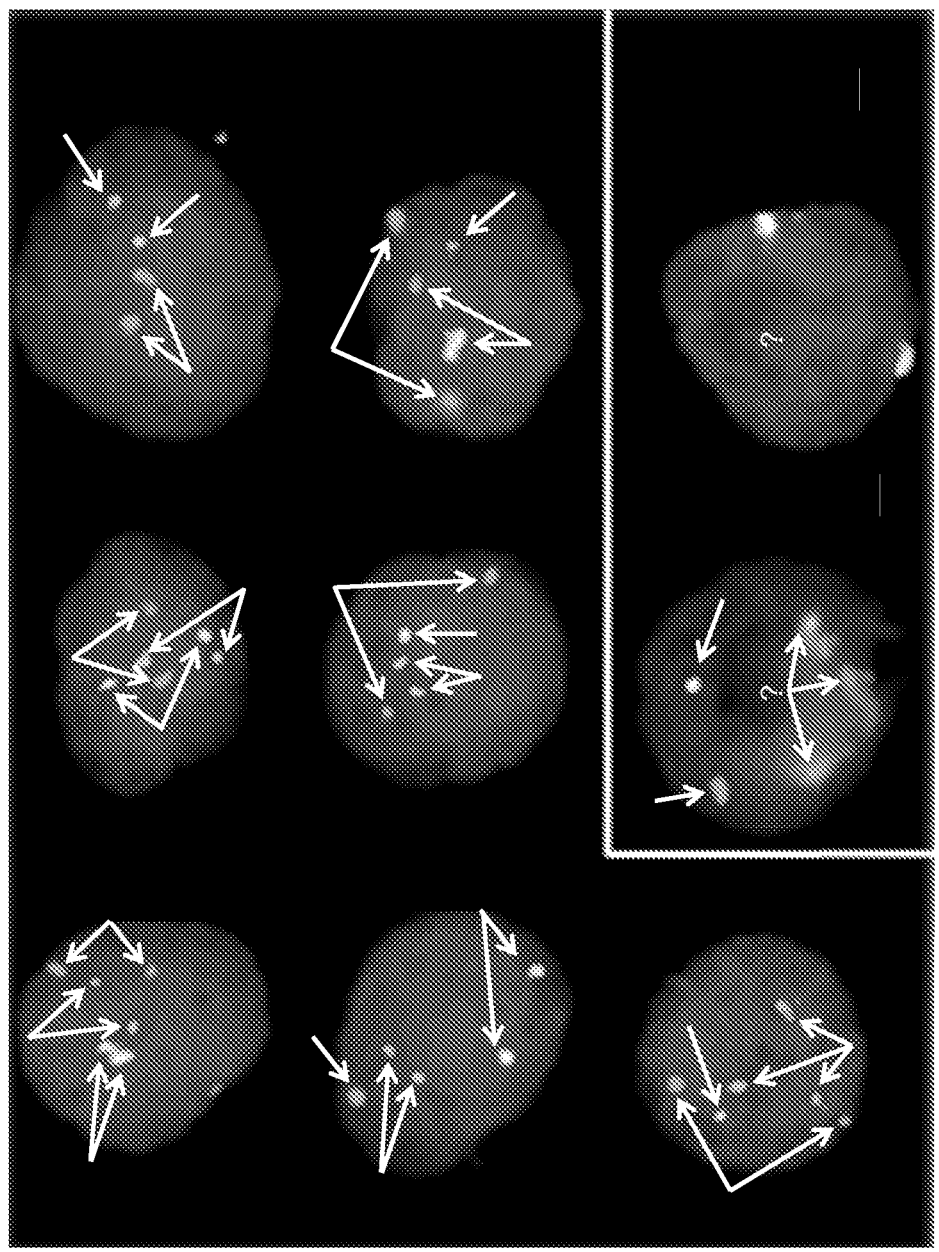
FIG. 13 is a series of images depicting three color SLP analyses of nine fixed non-neoplastic lymph node cells. For each panel, arrow connected at their bases point to signals of the same color in the original photomicrograph. Single arrows indicate signals that were present in only one copy in the original photomicrograph. Seven of these cells presented with signals for all three probes that were able to be scored and the score of each of the three probes is indicated. Two of the cells (boxed; lower middle and right) are shown as examples of cells that produced data that were not scorable for the green signal (triple arrow identified with a "?") or any of the three signals (right). As with non-fixed cells, scores of fixed cells indicated a frequency of n=1 for up to 3% of cells counted.
Figure 14:
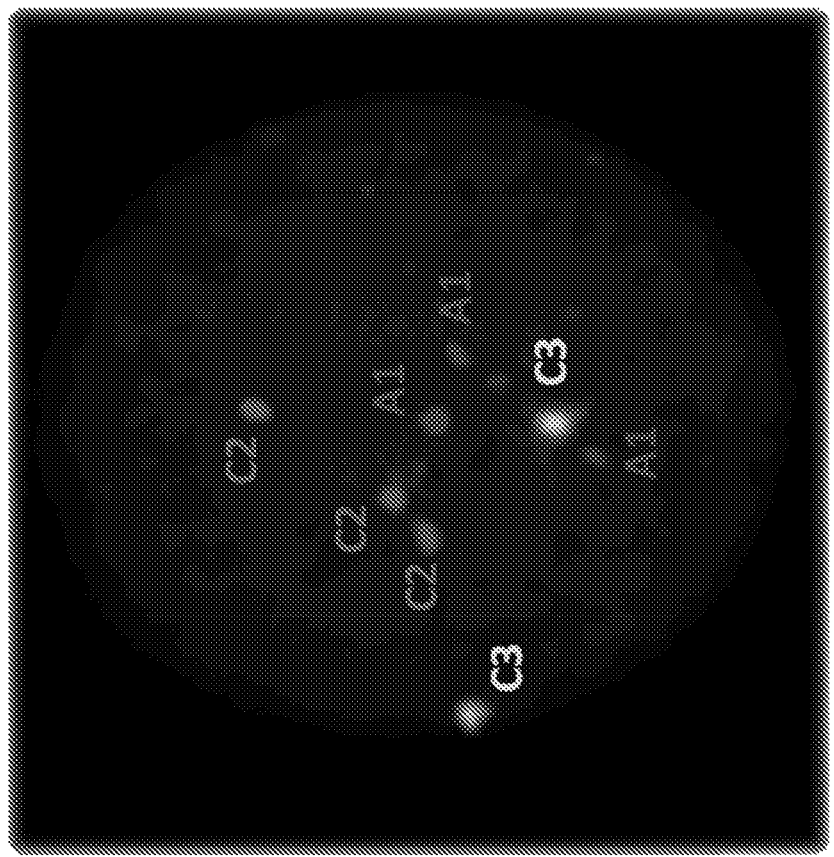
FIG. 14 is an example of four loci, multicolor FISH analysis of canine interphase nuclei. The left panel is an image of a control, non-neoplastic cell showing two copies of each of the four loci being evaluated for chromosome regions A1 (red in the original photomicrograph), A2 (orange in the original photomicrograph), C2 (purple in the original photomicrograph), and C3 (green in the original photomicrograph). The right panel is an image of a neoplastic nucleus from a canine lymphoma biopsy specimen probed simultaneously with the same four probes. In this cell, though there were two copies of the locus labeled with the green fluorophore in the original photomicrograph (labeled C3 in this panel), there were three copies each of the probes labeled with the red fluorophore in the original photomicrograph (labeled A1) and purple fluorophore in the original photomicrograph (labeled C2). There were no retained copies of the marker labeled with the orange fluorophore in the original photomicrograph (probe A2). Counts were made from >50 cells and the mean copy number of each locus was determined and collated.
Figure 14:
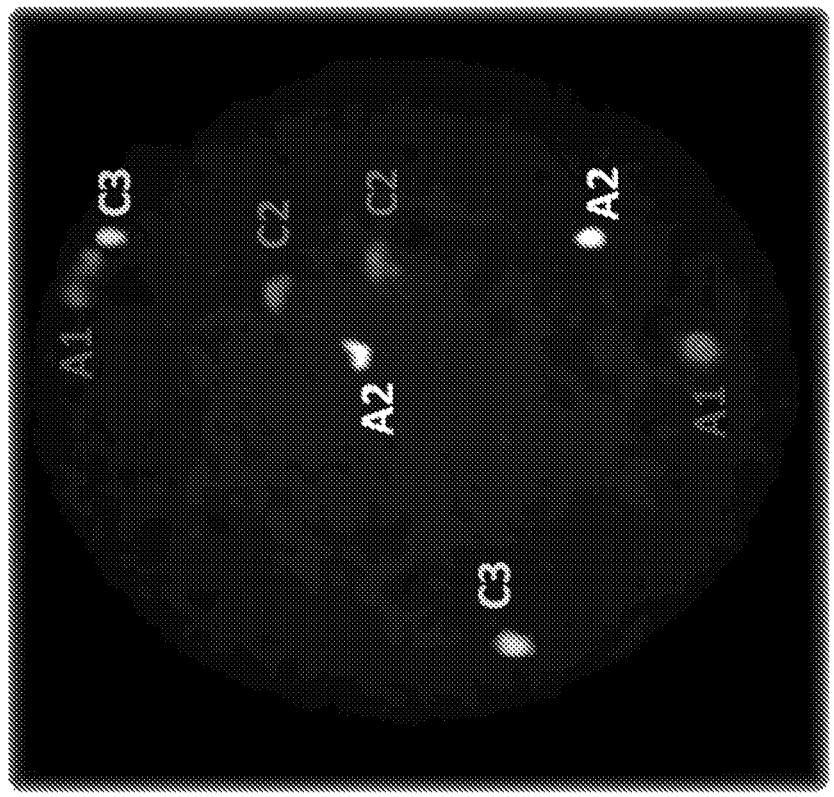

In fixed nuclei, higher background noise restricted the successful interpretation to three to four colors, so the ten loci were evaluated in three reactions: two containing three loci and the third containing four probes. See FIGS. 13 and 14. As with unfixed nuclei, there was a small percentage of cells that were deleted for one copy of probes assessed. This could have been due to spontaneous aberration in the non-neoplastic cells and/or to the inability of the probe(s) to access the complimentary sequence(s) within the nuclei.

The mean copy number of chromosome region A1 was determined to be positively associated with DFI: the higher the mean copy number, the longer the duration of first remission and thus survival. This association can also be valid in multi-agent chemotherapy protocols. Of particular interest was the high proportion of cells that had three copies (trisomy) of the loci on dog chromosomes 1 and 6. Canine chromosome 6 contains the gene TSC2, a gene involved in the regulation of cancers.

Testing Sample Population (n=121).

Initially, 121 of the 322 patient samples were selected randomly. Cells from these 121 cases were evaluated initially for DNA copy number at ten loci using multicolor fluorescence in situ hybridization (FISH) protocols. For this process, a series of overlapping canine bacterial artificial chromosome (BAC) clones were identified that resided in the middle of each of the regions each of interest. These were used in FISH assays to determine the copy number of each of the ten loci in up to fifty cells derived from each case. The mean copy number of each locus within each patient was then calculated and statistical analysis was used to identify any correlation between mean DNA copy number and disease free interval.

One probe (C4) had an unacceptable background and so was set aside for further development. The remaining nine (9) probes (designated as A1-A3, B1-B3, and C1-C3) were each considered for association to disease free interval (DFI). A regression model was developed that included potential multivariate risk models. Random Forests with cross-validation was used to perform variable selection for the model, such that from the nine potential predictor variables, only those variables that were robust predictors were included in the final model.

The results of this first set of 121 patients indicated a significant correlation between mean copy number of chromosome region A1 (i.e., canine chromosome 1; CFA1) and disease free interval. The coefficient for the A1 mean was 334, indicating that for every 1.0 increase in copy number, the expected value of disease free interval (DFI) increased by 334 days. Univariate linear regression analysis for chromosome region A1 resulted in a significant regression model associating chromosome region A1 with DFI as follows:

$$DFI = 333.8438 \times (\text{mean copy number value for } A1) - 342.4995 \text{ days} \quad \text{Formula I}$$

This regression explained 9.65% of the variation in DFI and the mean predicted DFI based on various mean values for chromosome region A1 are presented in Table 3, along with the corresponding ranges of predicted survival times at the 95% Confidence Interval.

TABLE 3

Prediction of Mean DFI based on Assessment of Mean Copy Number of Chromosome Region A1

| A1 MEAN VALUE | MEAN DFI (days) | 95% Confidence Interval (days) |
| --- | --- | --- |
| 1.5 | 158.27 | 59.408 to 257.12 |
| 1.75 | 241.73 | 176.86 to 306.59 |
| 2.0 | 325.19 | 271.77 to 378.61 |
| 2.25 | 408.65 | 333.08 to 484.22 |
| 2.5 | 492.11 | 379.06 to 605.16 |
| 3.0 | 659.03 | 460.16 to 857.91 |

The results of this first set of 121 patients also indicated a significant correlation between mean copy number of chromosome region C2 (i.e., canine chromosome 6; CFA6) and disease free interval. The coefficient for the chromosome region C2 mean was 253, indicating that for every 1.0 increase in copy number, the expected value of disease free interval increased by 253 days. Univariate linear regression analysis for chromosome region C2 resulted in a significant regression model associating chromosome region C2 with DFI as follows:

$$DFI = 253.0157 \times (\text{mean copy number value for } C2) - 146.2368 \text{ days} \quad \text{Formula II}$$

This regression explained 3.75% of the variation in DFI and the mean predicted DFI based on various mean values for C2 are presented in Table 4, along with the corresponding ranges of predicted survival times at the 95% Confidence Interval.

TABLE 4

Prediction of Mean DFI based on Assessment of Mean Copy Number of Chromosome Region C2

| C2 MEAN VALUE | MEAN DFI (days) | 95% Confidence Interval (days) |
| --- | --- | --- |
| 1.5 | 233.29 | 139.61 to 326.97 |
| 1.75 | 296.54 | 237.35 to 355.73 |
| 2.0 | 359.79 | 287.16 to 432.43 |
| 2.25 | 423.05 | 304.34 to 541.76 |
| 2.5 | 486.3 | 313.23 to 659.38 |
| 3.0 | 612.81 | 325.04 to 900.58 |

Using mean copy number of the first 121 cases, two of the nine loci (chromosome regions A1 and C2) were selected as significant predictors of outcome (chromosome region A1 was more significant than chromosome region C2). The tree modeling indicated a two-variable model with chromosome region A1 (CFA 1: nucleotides 116,839,835 to 117,635,991) and chromosome region C2 (CFA6: nucleotides 41,565,280 to 42,426,757) that was slightly more predictive than chromosome region A1 alone. This suggested that consideration of the mean copy number of this region of CFA6 added to the predictive power of CFA1. Permutation testing indicated a significant two-variable model that predicted disease free interval, involving chromosome regions A1 and C2. The regression model developed was as follows:

$$DFI = 327.0698 \times (\text{mean copy number value for } A1) + 239.0605 \times (\text{mean copy number value for } C2) - 762.4566 \text{ days} \quad \text{Formula III}$$

The regression equation predicted survival based on the mean copy number of probes A1 and C2. It is possible that the slope of the regression might change as additional data are added, and thus the presently disclosed subject matter is based at least in part on identifying the strong association between chromosome region A1 and/or chromosome region C2 with DFI. Additional examples of prediction using the approaches disclosed herein are provided in Table 5.

TABLE 5

Prediction of Mean DFIs Based on Assessments of Mean Copy Numbers of Chromosome Regions A1 and C2 in the Canine Genome

| A1 & C2 MEAN VALUE | MEAN DFI (days) | 95% Confidence Interval (days) |
| --- | --- | --- |
| 1.5 | 90 | 0-212 |
| 1.75 | 232 | 164-300 |
| 2.0 | 374 | 304-444 |
| 2.25 | 515 | 390-660 |
| 2.5 | 657 | 464-849 |
| 3.0 | 941 | 607-1274 |

The data in Table 5 assumed that the mean copy numbers for both chromosome regions A1 and C2 were the same, and this can also be modified if either of the values were to changes. In a normal, non-cancerous dog, a copy number of 2 would be expected.

The data presented herein indicated that the mean DNA copy number of chromosome regions A1 (CFA1) and C2 (CFA6) were able to predict disease free interval in dogs diagnosed with lymphoma that are receiving therapy, as an example doxorubicin (supplemented with L-asparaginase). Since commonly employed multi-agent chemotherapy typically comprises administration of doxorubicin, similar results should be found in dogs treated with multi-agent chemotherapy.

Replication Sample Population (n=39).

The mean copy numbers of chromosome regions A1 and C2 were evaluated in a subsequent set of 39 additional cases (replication set) from the study population. Evaluation of these 39 cases indicated a significant correlation between mean copy number of chromosome region A1 (La, canine chromosome 1; CFA1) and disease free interval. The significant association of the region defined by chromosome region A1 thus remained in this replication set and when combined with the previous 121 cases, a new regression analysis based on all 150 cases generated Formula A, as follows:

$$DFI = 374.1685 \times (\text{mean copy number value for } A1) - 438.7572 \text{ days} \quad \text{Formula A}$$

This regression explained 12.08% of the variation in DFI. The mean predicted DFI based on various mean values for chromosome region A1 are presented in Table 6, along with the corresponding ranges of predicted survival times at the 95% Confidence Interval.

TABLE 6

Prediction of Mean DFI Based on Assessment of Mean Copy Number of Chromosome Region A1 in the Canine Genome

| A1 MEAN VALUE | MEAN DFI (days) | 95% Confidence Interval (days) |
|---|---|---|
| 1.5 | 122.5 | 36.505 to 208.49 |
| 1.75 | 216.04 | 159.56 to 272.51 |
| 2.0 | 309.58 | 263.95 to 355.21 |
| 2.25 | 403.12 | 339.31 to 466.94 |
| 2.5 | 496.66 | 400.96 to 592.37 |
| 3.0 | 683.75 | 514.55 to 852.94 |

Evaluation of the 39 cases comprising the replication set did not indicate a significant correlation between mean copy number of chromosome region C2 (La, canine chromosome 6; CFA6) and disease free interval. The significant association of the region defined by chromosome region C2 thus did not remain evident in this replication set. This is likely due to the small sample size of the replication set. When all 150 cases were analyzed, chromosome region C2 remained a significant predictor of DFI.

Compilation of all data for chromosome regions A1 and C2 in all 150 cases (testing set+replication set) and subsequent regression analysis with both the chromosome region A1 and the chromosome region C2 variables generated the new regression equation, Formula AC, as follows:

DFI=367.5094×(mean copy number value for $A1$)+ 228.2709×(mean copy number value for $C2$)− 839.22 days     Formula AC This regression explained 14.52% of the variation in DFI. Tests of significance indicated a highly significant association ($p<0.0001$) for the chromosome region A1 variable coefficient and a significant association ($p<0.030$) for the chromosome region C2 variable coefficient. This is a nominal level of significance for chromosome region C2, indicating that it is not nearly as predictive as A1.

This equation was used to generate the mean DFI ranges of predicted survival times at the 95% Confidence Interval for the combined data set (see Table 7).

TABLE 7

Prediction of Mean DFI Based on Assessment of Mean Copy Numbers of Chromosome Regions A1 and C2 in the Canine Genome

| MEAN VALUE OF BOTH A1 and C2 | MEAN DFI (days) | 95% Confidence Interval (days) |
|---|---|---|
| 1.5 | 54.449 | −55.462 to 164.36 |
| 1.75 | 203.39 | 142.48 to 264.31 |
| 2.0 | 352.34 | 294.72 to 409.96 |
| 2.25 | 501.28 | 396.85 to 605.72 |
| 2.5 | 650.23 | 487.52 to 812.94 |
| 3.0 | 948.12 | 662.56 to 1233.7 |

The test, in some embodiments, is based on molecular cytogenetic evaluation of cells derived from lymph nodes of dogs diagnosed with lymphoma.

Example 4

Statistical Analyses

Univariate Screening.

Raw data for the 121 case set were collapsed into summary measures for the nine (9) markers genotyped. The summary measures derived were as follows: number of samples evaluated, mean copy number per sample, and proportion of samples per individual with copy number gains. Colinearity between markers was evaluated by examining correlations, as shown in Table 8. Significant correlations are indicated by asterisks. The results indicated significant correlations between chromosome regions A1 and C1, as well as between chromosome regions C1 and C2.

TABLE 8

Correlation Matrix for the Nine CNV Markers Genotyped (Mean Values)

|  | A1 | A2 | A3 | B1 | B2 | B3 | C1 | C2 |
|---|---|---|---|---|---|---|---|---|
| A2 | 0.24 | 1.0 | — | — | — | — | — | — |
| A3 | 0.04 | 0.0001 | 1.0 | — | — | — | — | — |
| B1 | 0.01 | 0.16 | −0.04 | 1.0 | — | — | — | — |
| B2 | 0.14 | 0.10 | 0.01 | 0.13 | 1.0 | — | — | — |
| B3 | 0.13 | −0.15 | −0.003 | 0.20 | 0.10 | 1.0 | — | — |
| C1 | 0.30* | 0.04 | 0.11 | −0.13 | −0.02 | 0.16 | 1.0 | — |
| C2 | 0.04 | −0.10 | 0.13 | −0.03 | 0.08 | 0.28 | 0.32* | 1.0 |
| C3 | 0.10 | −0.11 | 0.20 | −0.12 | −0.06 | 0.08 | 0.13 | 0.39* |

Asterisks indicate significant correlations ($p < 0.05$) of mean values after Bonferroni correction for multiple testing.

Mean copy number for each marker was tested for significant correlation with the number of samples evaluated, to evaluate potential technical confounding. After Bonferroni correction for multiple testing, mean copy number of chromosome region A1 was found to be significantly correlated ($p<0.001$) with the number of samples collected. No other markers demonstrated significant correlations with the number of samples. Based on this result, significant association results were evaluated in context of this correlation.

Univariate linear regression was performed to evaluate the association between the mean copy number of each individual genetic marker and the disease free interval. Each genetic marker was independently evaluated in a regression model to predict the disease free interval. Table 9 lists the summary statistics for the regression results for the mean copy number of each marker, based on the first 121 cases. See discussion under "Scoring Archival Samples" in Example 3 above. After a Bonferroni correction for multiple comparisons, marker A1 was significantly associated with disease free interval.

TABLE 9

$R^2$, Root Mean Square Error, and p Value for an Exemplary Regression Model for the Mean Copy Number of Each Variant and DFI

| Variant | $R^2$ | Root Mean Square Error | p value |
|---|---|---|---|
| A1 | 0.0965 | 296.27 | 0.0005 |
| A2 | 0.0118 | 317.28 | 0.2497 |
| A3 | 0.0223 | 290.51 | 0.1077 |
| B1 | 0.004 | 319.51 | 0.4851 |
| B2 | 0.0231 | 295.9 | 0.1213 |
| B3 | 0.0226 | 318.84 | 0.1337 |
| C1 | 0.0031 | 317.81 | 0.5593 |
| C2 | 0.0375 | 312.28 | 0.0390 |
| C3 | 0.0033 | 329.72 | 0.5661 |

The univariate regression analysis was repeated using the proportion of samples collected per individual with copy number gains as potential predictors, and no results were significant at either a nominal level, or at a Bonferroni corrected level.

Predictive Modeling.

Regression trees were built, with each variant as a potential predictive attribute (variable), weighted for the number of samples collected per individual. Ten-fold cross-validation was used to evaluate the predictive ability of the model, and to perform pruning (variable selection). Pruning was performed according to the following steps, based on optimizing the root mean square error of the model divided by the global standard deviation:

1) fit a full regression model, with all potential attributes included;
2) remove the attribute that contributes least to the equation (because it has the smallest weight when the attributes are converted to a common scale);
3) if the resulting equation has a lower estimated error rate, keep the attribute out and repeat the process on the remaining attributes, otherwise, put the attribute back in and stop the process.

Analysis of the data from the testing set of 121 cases identified two significant markers, A1 and C2, that were highly significantly associated with DFI (p<0.0018) and in combination explained 31.06% of the variation in DFI.

Permutation testing was used to empirically asses the statistical significance of the resulting model. This analysis indicated a significant two-variable model that predicted disease free interval, involving chromosome regions A1 and C2. The regression model developed was as follows:

$$DFI=327.0698\times(\text{mean copy number value for }A1)+239.0605\times(\text{mean copy number value for }C2)-762.4566 \text{ days} \quad \text{Formula III}$$

The summary statistics for the final model were as follows: correlation coefficient=0.247; class complexity|order 0=708.7276 bits (5.8573 bits/instance); class complexity|scheme=20722.0186 bits (171.2564 bits/instance); Complexity improvement (Sf)=−20013.291 bits and =−165.3991 bits/instance. Mean absolute error=206.9582; Root mean squared error=302.8203; relative absolute error=93.9909%; root relative squared error=97.574%.

Random Forest™.

The RANDOM FOREST™ classification and regression tool (Breiman (2001) Random Forests. *Machine Learning* 45(1):5-32) was investigated for predicting a compound's quantitative or categorical biological activity based on a quantitative description of the compound's molecular structure. RANDOM FOREST™ is an ensemble of unpruned classification or regression trees created by using bootstrap samples of the training data and random feature selection in tree induction. Prediction is made by aggregating (majority vote or averaging) the predictions of the ensemble. RANDOM FOREST™ is a tool capable of delivering performance that is among the most accurate methods to date.

Replication.

In order to further evaluate this model, a replication set of data (n=29) was collected to test the predictive power of these two markers in an independent, separate sample. In the replication sample, chromosome region A1 remained highly significantly associated with survival outcome (p<0.002), but chromosome region C2 was not (p>0.05), likely due to much lower sample size and lower power of this locus. These data demonstrated the highly robust nature of chromosome region A1 as a predictor of response to therapy.

Data from this second set of 29 patients independently also revealed a strong association between the mean copy number of chromosome region A1 and DFI. By combining all cases evaluated to date the total number is 150 and analysis of chromosome region A1 in this larger cohort generated the regression as shown below.

The overall regression model was still significant with the coefficient for chromosome region A1 mean significant at p<0.0001. The revised significant regression model associating chromosome region A1, based on all 150 cases (see Example 3, Table 6 above), was as follows:

$$DFI=374.1685\times(\text{mean copy number value for }A1)-438.7572 \text{ days} \quad \text{Formula A}$$

The coefficient for the A1 mean was 374.1685, indicating that for every 1.0 increase in copy number, the expected value of disease free interval increased by 374.1685 days.

Table 10 provides a prediction of mean disease free intervals (days) and the ranges associated with the 95% Confidence Intervals, based on an assessment of the mean copy number of chromosome region A1 in the canine genome, using the combined (n=150) dataset (original (n=121) plus the replication (n=29)) samples considering only the chromosome region A1 variable. The regression equation used to generate the data presented in Table 10 was Formula A as follows:

$$DFI=374.1685\times(\text{mean copy number value for }A1)-438.7572 \text{ days} \quad \text{Formula A}$$

TABLE 10

Prediction of Mean DFI Based on Assessment of Mean Copy Number of Chromosome Region A1 in the Canine Genome in the Combined Data Set

| A1 MEAN VALUE | MEAN DFI (days) | 95% Confidence Interval (days) |
|---|---|---|
| 1.5 | 122.5 | 36.505 to 208.49 |
| 1.75 | 216.04 | 159.56 to 272.51 |
| 2.0 | 309.58 | 263.95 to 355.21 |
| 2.25 | 403.12 | 339.31 to 466.94 |
| 2.5 | 496.66 | 400.96 to 592.37 |
| 3.0 | 683.75 | 514.55 to 852.94 |

The regression data presented in Table 10 explained 12.08% of the variation in DFI.

Regression analysis on only the C2 variable using the combined dataset (n=150 patients), generated the following revised regression equation (p<0.014):

$$DFI=271.4727\times(\text{mean copy number value for }C2)-199.6737 \text{ days} \quad \text{Formula C}$$

This regression explained 4.01% of the variation in DFI.

Combining data for chromosome regions A1 and C2 for all 150 cases generated the following regression (Formula AC) when both regions were considered.

$$DFI=367.50949\times(\text{mean copy number value for }A1)+228.2709\times(\text{mean copy number value for }C2)-839.22 \text{ days} \quad \text{Formula AC}$$

This regression explained 14.52% of the variation in DFI. Tests of significance indicated p<0.0001 for the A1 variable coefficient and p<0.030 for the C2 variable coefficient. While this is a nominal level of significance for C2, C2 was not as predictive as A1. Examples of mean DFI and corresponding values at 95% Confidence Interval are shown in Table 11, assuming the values for mean A1 and mean C2 are the same.

TABLE 11

Prediction of Mean DFI Based on Assessment of Mean Copy Number of Chromosome Regions A1 and C2 in the Canine Genome in the Combined Data Set

| MEAN VALUE OF BOTH A1 and C2 | MEAN DISEASE FREE INTERVAL (days) | 95% Confidence Interval (days) |
|---|---|---|
| 1.5 | 54.449 | −55.462 to 164.36 |
| 1.75 | 203.39 | 142.48 to 264.31 |

TABLE 11-continued

Prediction of Mean DFI Based on Assessment of Mean Copy Number of Chromosome Regions A1 and C2 in the Canine Genome in the Combined Data Set

| MEAN VALUE OF BOTH A1 and C2 | MEAN DISEASE FREE INTERVAL (days) | 95% Confidence Interval (days) |
|---|---|---|
| 2.0 | 352.34 | 294.72 to 409.96 |
| 2.25 | 501.28 | 396.85 to 605.72 |
| 2.5 | 650.23 | 487.52 to 812.94 |
| 3.0 | 948.12 | 662.56 to 1233.7 |

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for predicting the disease free time interval for a subject with a cancer under consideration for initial or further chemotherapy treatment, the method comprising:
    obtaining a biological sample from a canine or human subject, wherein the sample comprises a number of cells;
    detecting a copy number of chromosome region A1, chromosome region C2, or both chromosome region A1 and chromosome region C2 in the biological sample, wherein the detecting comprises contacting the chromosome region A1 with a first plurality of probes and/or the chromosome region C2 with a second plurality of probes, wherein the first and the second plurality of probes are labeled with different fluorescent labels, and differentially visualizing the chromosome region A1 and/or the chromosome region C2 in the biological sample by multicolor fluorescence in situ hybridization (FISH);
    and further wherein:
        in canines, chromosome region A1 comprises nucleotides 116,839,835-117,635,991 of canine chromosome 1 (CFA1) as set forth in Accession No. NC 006583 of the GENBANK® biosequence database and chromosome region C2 comprises nucleotides 41,565,280-42,426,757 of canine chromosome 6 (CFA6) as set forth in Accession No. NC_006588 of the GENBANK® biosequence database; and
        in humans, chromosome region A1 comprises nucleotides 43,452,745-44,221,900 of human chromosome 19 as set forth in Accession No. NC_000019 of the GENBANK® biosequence database and chromosome region C2 comprises nucleotides 1,629,295-2,350,975 of human chromosome 16 as set forth in Accession No. NC_000016 of the GENBANK® biosequence database;
    dividing the copy number detected for the chromosome region A1 and/or the copy number detected for the chromosome region C2 by the number of cells in the biological sample to obtain a mean copy number value for chromosome region A1, a mean copy number value for chromosome region C2, or a mean copy number value for chromosome region A1 and a mean copy number value for chromosome region C2; and
    correlating the mean copy number value(s) obtained for chromosome region A1 and/or chromosome region C2 with a duration of disease free interval.

2. The method of claim 1, wherein the subject has lymphoma.

3. The method of claim 2, wherein the lymphoma is non-Hodgkin's lymphoma.

4. The method of claim 1, wherein the subject is a canine.

5. The method of claim 1, wherein the biological sample comprises a biopsy.

6. The method of claim 1, wherein the biological sample comprises lymph node cells.

7. The method of claim 1, wherein the chemotherapy treatment comprises administering doxorubicin to the subject.

8. The method of claim 7, wherein the chemotherapy treatment further comprises administering L-asparaginase to the subject.

9. The method of claim 1, further comprising determining the disease free interval (DFI) by substituting the mean copy number value for A1 into Formula A, wherein Formula A is:

$$DFI=374.1685\times(\text{mean copy number value for }A1)-438.7572 \text{ days.}$$

10. The method of claim 1, comprising:
    detecting a copy number of chromosome region C2 in the biological sample; and
    dividing the copy number by the number of cells in the biological sample to obtain a mean copy number value for C2.

11. The method of claim 10, wherein the detecting a copy number of chromosome region C2 comprises contacting the sample with a probe able to detect the presence of chromosome region C2 under conditions sufficient to enable hybridization of the probe to chromosome region C2.

12. The method of claim 10, further comprising determining the disease free interval (DFI) by substituting the mean copy number value for A1 and the mean copy number value for C2 into Formula AC, wherein Formula AC is:

$$DFI=367.5094\times(\text{mean copy number value for }A1)+228.2709\times(\text{mean copy number value for }C2)-839.22 \text{ days.}$$

13. The method of claim 1, wherein a mean copy number has a positive correlation with an increased disease free time interval.

14. A kit for predicting disease free time interval in a canine or human subject with lymphoma under consideration for initial or further chemotherapy treatment, the kit comprising a first probe able to detect chromosome region A1 and a second probe able to detect chromosome region C2, wherein:
    the first probe and the second probe are labeled with different fluorescent labels that allow differential visualization of the chromosome region A1 and the chromosome region C2 in the biological sample by multicolor fluorescence in situ hybridization (FISH); and
    in canines, chromosome region A1 comprises nucleotides 116,839,835-117,635,991 of canine chromosome 1 (CFA1) as set forth in Accession No. NC_006583 of the GENBANK® biosequence database and chromosome region C2 comprises nucleotides 41,565,280-42,426,757 of canine chromosome 6 (CFA6) as set forth in Accession No. NC_006588 of the GENBANK® biosequence database; and in humans, chromosome region A1 comprises nucleotides 43,452,745-44,221,900 of human chromosome 19 as set forth in Accession No. NC_000019 of the GENBANK® biosequence database and chromosome region C2 comprises nucleotides 1,629,295-2,350,975 of human chromosome 16 as set forth in Accession No. NC_000016 of the GENBANK® biosequence database.

15. A computer readable storage medium having stored thereon computer executable instructions that, when executed by a processor of a computer, control the computer to perform steps comprising:

analyzing a mean copy number from chromosome region A1, a mean copy number value for chromosome region C2, or mean copy number values for both chromosome region A1 and chromosome region C2 from a biological sample obtained from a canine or human subject with a cancer, wherein:

in canines, chromosome region A1 comprises nucleotides 116,839,835-117,635,991 of canine chromosome 1 (CFA1) as set forth in Accession No. NC 006583 of the GENBANK® biosequence database and chromosome region C2 comprises nucleotides 41,565,280-42,426,757 of canine chromosome 6 (CFA6) as set forth in Accession No. NC 006588 of the GENBANK® biosequence database; and in humans, chromosome region A1 comprises nucleotides 43,452,745-44,221,900 of human chromosome 19 as set forth in Accession No. NC_000019 of the GENBANK® biosequence database and chromosome region C2 comprises nucleotides 1,629,295-2,350,975 of human chromosome 16 as set forth in Accession No. NC_000016 of the GENBANK® biosequence database; and outputting a predicted disease free interval (DFI) for the canine or human subject.

16. The computer readable storage medium of claim 15, wherein the processor employs Formula A to compute the DFI, and further wherein Formula A is:

$$DFI = 374.1685 \times (\text{mean copy number value for } A1) - 438.7572 \text{ days}.$$

17. The computer readable storage medium of claim 15, comprising instructions that control the computer to perform steps comprising analyzing a mean copy number from chromosome region C2 from the biological sample.

18. The computer readable storage medium of claim 17, wherein the processor employs Formula AC to compute the DFI, and further wherein Formula AC is:

$$DFI = 367.5094 \times (\text{mean copy number value for } A1) + 228.2709 \times (\text{mean copy number value for } C2) - 839.22 \text{ days}.$$

* * * * *